United States Patent [19]
Purdy et al.

[11] Patent Number: 5,562,729
[45] Date of Patent: Oct. 8, 1996

[54] HEART VALVE

[75] Inventors: David L. Purdy, Marion Center; James R. Cupp, Indiana; Frederick J. Shipko, Spring Church; Robert D. Norman, Clymer, all of Pa.

[73] Assignee: Biocontrol Technology, Inc., Pittsburgh, Pa.

[21] Appl. No.: 332,720

[22] Filed: Nov. 1, 1994

[51] Int. Cl.$^6$ ........................................ A61F 2/24
[52] U.S. Cl. ................................ 623/2; 623/900
[58] Field of Search ................................ 623/2, 900

[56] References Cited

U.S. PATENT DOCUMENTS

| | | | |
|---|---|---|---|
| 3,118,468 | 1/1964 | Bochan | 623/2 |
| 3,656,185 | 4/1972 | Carpentier | 3/1 |
| 3,755,823 | 9/1973 | Hancock | 3/1 |
| 4,055,861 | 11/1977 | Carpentier et al. | 3/1.5 |
| 4,056,854 | 11/1977 | Boretos et al. | 623/2 |
| 4,084,268 | 4/1978 | Ionescu et al. | 623/2 |
| 4,106,129 | 8/1978 | Carpentier et al. | 623/2 |
| 4,222,126 | 9/1980 | Boretos et al. | 3/1.5 |
| 4,254,773 | 3/1981 | Waldbillig | 128/348 |
| 4,265,694 | 5/1981 | Boretos et al. | 156/242 |
| 4,441,216 | 4/1984 | Ionescu et al. | 3/1.5 |
| 4,451,936 | 6/1984 | Carpentier et al. | 3/1.5 |
| 4,470,157 | 9/1984 | Love | 623/2 |
| 4,490,859 | 1/1985 | Black et al. | 623/2 |
| 4,501,030 | 2/1985 | Lane | 3/1.5 |
| 4,510,628 | 4/1985 | Kolff | 3/1.5 |
| 4,549,879 | 10/1985 | Groshong et al. | 604/247 |
| 4,569,675 | 2/1986 | Prosi et al. | 604/175 |
| 4,573,978 | 3/1986 | Reilly | 604/240 |
| 4,586,928 | 5/1986 | Barnes et al. | 604/408 |
| 4,605,407 | 8/1986 | Black et al. | 623/2 |
| 4,655,225 | 4/1987 | Dähne et al. | 128/633 |
| 4,662,357 | 5/1987 | Pierce et al. | 128/1 |
| 4,676,241 | 6/1987 | Webb et al. | 128/207.14 |
| 4,685,905 | 8/1987 | Jeanneret nee Aab | 604/247 |
| 4,731,074 | 3/1988 | Rousseau et al. | 623/2 |
| 4,778,461 | 10/1988 | Pietsch et al. | 623/2 |
| 4,800,603 | 1/1989 | Jaffe | 8/94.11 |
| 4,874,378 | 10/1989 | Hillstead | 604/167 |
| 4,881,761 | 11/1989 | Hornlein et al. | 285/239 |
| 4,886,502 | 12/1989 | Poirier et al. | 604/175 |
| 4,888,009 | 12/1989 | Lederman et al. | 623/2 |
| 4,892,518 | 1/1990 | Cupp et al. | 604/93 |
| 4,975,581 | 12/1990 | Robinson et al. | 250/339 |
| 5,070,874 | 12/1991 | Barnes et al. | 128/633 |
| 5,073,171 | 12/1991 | Eaton | 604/266 |
| 5,171,271 | 12/1992 | Furcht et al. | 623/11 |
| 5,207,707 | 5/1993 | Gourley | 623/2 |

FOREIGN PATENT DOCUMENTS

| | | |
|---|---|---|
| 0193987 | 9/1986 | European Pat. Off. . |
| 0200926 | 11/1986 | European Pat. Off. . |
| 3130646 | 2/1983 | Germany . |
| 3248560 | 7/1984 | Germany . |
| 3614292 | 11/1987 | Germany . |

OTHER PUBLICATIONS

"Thoracic and Cardiovascular Surgery", Jan. 1983, vol. 85, No. 1, cover page & 2 pages.

MediPort by Cormed, Inc. brochure, pp. 2–8 (no date available).

Infuse–A–Port by Infusaid brochure from the Physician's Manual, cover page & 7 pages. (no date available).

*Primary Examiner*—Michael J. Milano
*Attorney, Agent, or Firm*—Webb Ziesenheim Bruening Logsdon Orkin & Hanson, P.C.

[57] ABSTRACT

A multi-leaflet (usually trileaflet) heart valve composed of biocompatible polymer which, in all of its embodiments, simultaneously imitates the structure and dynamics of biological heart valves and avoids promotion of calcification. The valve includes a plurality of flexible leaflets dip cast on a mandrel, which leaflets are then bonded with a bonding agent to the interior surfaces of a plurality of struts on a metal-reinforced prosthetic stent. The leaflets open and close in response to the pumping action of the heart and, due to the design of the leaflets, fatigue resistance of the heart valve is high. The leaflets and the polymer components of the prosthetic stent are manufactured of biocompatible polymers exhibiting intrinsic calcification-resistant properties.

17 Claims, 16 Drawing Sheets

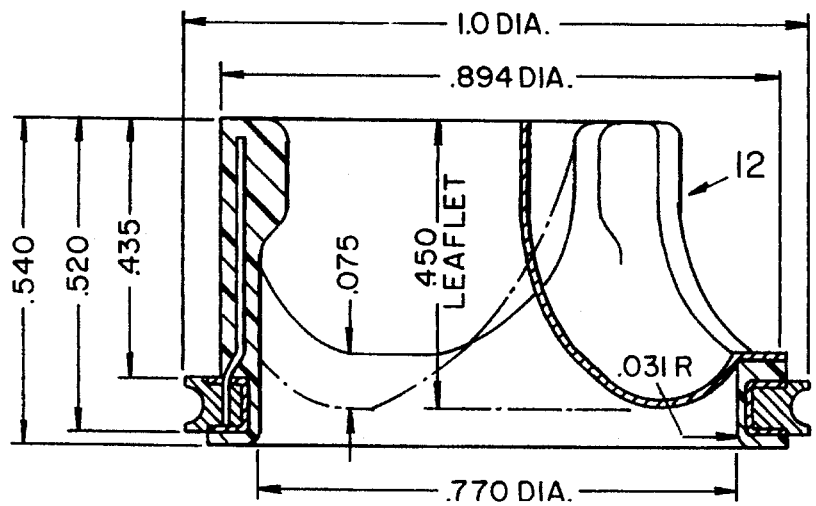
FIG. 15
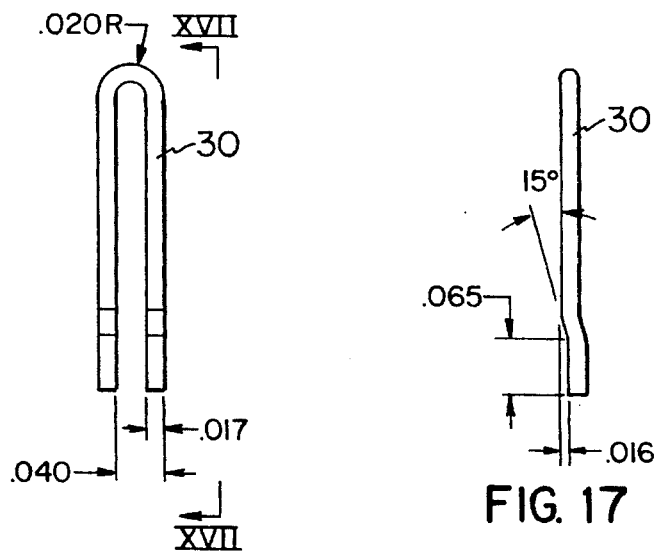
FIG. 16
FIG. 17
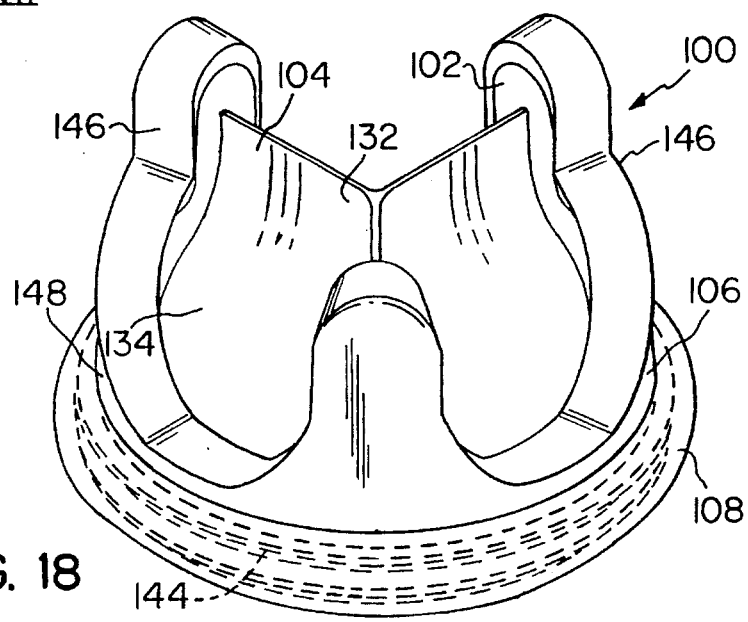
FIG. 18

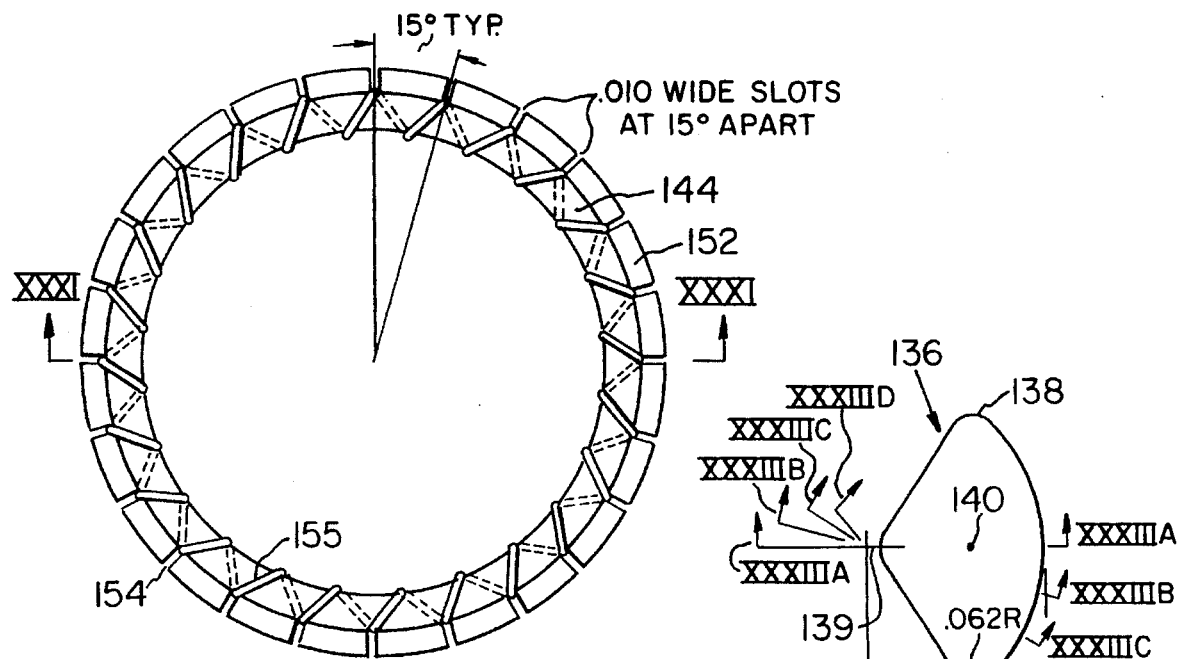
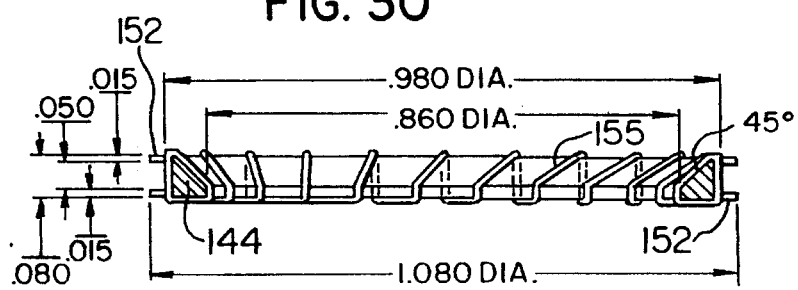
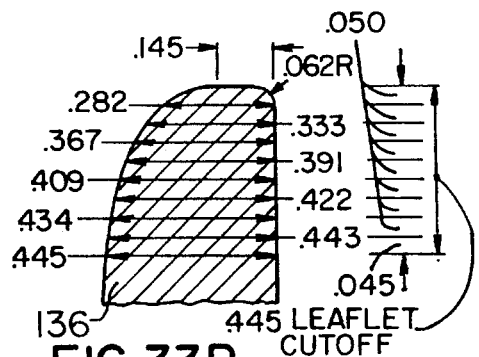
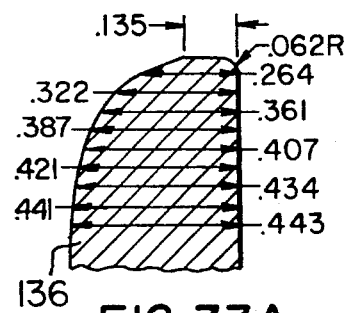
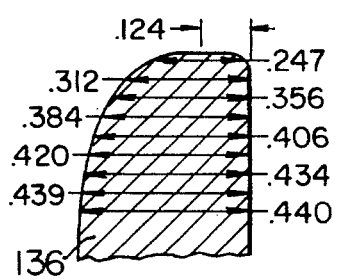
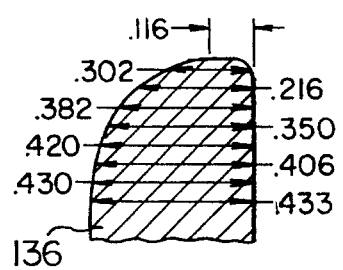

HEART VALVE

FIELD OF THE INVENTION

The present invention relates generally to prosthetic heart valves which can surgically replace a natural valve, usually the aortic or mitral valve, and which are designed both to maximize optimal blood flow and to prevent calcification or plaque formation.

BACKGROUND OF THE INVENTION

Disorders of the heart valves usually involve both stenosis and regurgitation. In cases of valve disease incident to juvenile rheumatic fever, for example, valvular damage occurs when anti-streptococcal antibodies attack valve tissue as well as the causal bacteria, inflaming the valve cusps and forming lesions. The lesions then, in time, fuse and narrow the opening of the valve. As the movement of the cusps of the valve becomes impaired, the valve can no longer seal properly when closed and therefore some blood leaks backward with each heartbeat. This narrowing of the opening and restriction of blood flow is known as stenosis; the backflow of blood is called regurgitation. Stenosis and regurgitation together result in net loss of blood flow volume. Serious valve disease leads predictably to cardiac insufficiency, cardiac failure and—unless otherwise forestalled—the death of the patient. Surgical repair of damage incident to valve disease has been and will continue to be an important area for improvement and innovation in the battle against heart disease.

SUMMARY OF THE PRIOR ACT

Effective surgical correction of heart valve disorders has been accomplished only comparatively recently. The first artificial heart valve was not successfully implanted until 1952. Valve design since that time has progressed from ball-and-cage valves to disc-in-cage valves to valves whose materials and structures more closely approximate those of the heart itself.

The human heart has four valves: the tricuspid valve which allows blood to enter the patient's right ventricle; the pulmonary valve which allows blood to leave the right ventricle through the pulmonary artery to the lungs; the mitral valve which allows blood to pass from the left atrium into the left ventricle; and the aortic valve which allows blood to leave the left ventricle and to flow into the body. While any of these valves may fail, failure usually occurs in the mitral and aortic valves since these experience the most severe loads. Most prosthetic valves are intended primarily as replacements for these two valves.

A wide variety of prior art prosthetic cardiac valves are known in the art, but the following are exemplary.

U.S. Pat. No. 4,222,126 to Boretos et al. discloses a polyurethane heart valve in which a semirigid frame (having a base ring and three struts) is unitary with an elastomeric membrane which forms the three leaflets of the valve. The leading edges of the leaflets are reinforced with a narrow elastomer band. A compliant base which is a permanent part of the valve body provides for attachment of the valve to the tissues of the heart.

U.S. Pat. No. 4,441,216 to Ionescu et al. discloses a heart valve in which the stent has narrow tipped stent legs and the material covering the stent is tissue—such as a preserved porcine aortic valve xenograft. U.S. Pat. No. 4,470,157 to Love discloses another heart valve which includes stents and a suture ring and which is intended for assembly with autogenous or foreign tissue.

U.S. Pat. No. 4,451,936 to Carpentier et al. discloses an aortic prosthetic device having a scalloped suture cuff to fit the Sinuses of Valsalva at the base of the aorta, and the valve itself has a base surface which curves between the intercommissural regions and the commissural supports.

U.S. Pat. No. 4,510,628 to Kolff discloses an artificial heart valve having thin, seamless leaflets which converge to the center of a frame from the frame's inner wall. The leaflets each have a convex outflow surface and a concave inflow surface. The leaflets meet along adjacent edges to form cusps.

U.S. Pat. No. 4,731,074 to Rousseau discloses a heart valve in which a rigid frame is covered with a fibre-reinforced matrix material membrane. Three synthetic leaflets are connected to the base of the frame and a coaptation area which is connected at its ends to a respective frame leg.

U.S. Pat. No. 4,778,461 to Pietsch et al. identifies a heart valve prosthesis including a support ring with at least two commissure supports and flexible cusps and being characterized by the height of the support rings' being less than the total height of the heart valve prosthesis.

U.S. Pat. No. 4,888,009 to Lederman et al. discloses a heart valve in which a suture ring surrounds a generally cylindrical body having curved flexible leaflets. The body and the leaflets are formed of flexible polymeric materials.

An ideal heart valve should: 1) duplicate the pressure drop experienced by the natural valve; 2) have an antithrombogenic character; 3) avoid damaging cellular blood components; 4) demonstrate fatigue resistance commensurate with the patient's life expectancy; 5) require no anticoagulation therapy; and 6) avoid the promotion of calcification. Even prior art heart valves which ostensibly satisfy features 1–3 and 5 (and not all do) are plagued by the problems of inadequate fatigue resistance and in vivo calcification. Moreover, optimization of characteristics 1–6 has never been achieved in the prior art heart valves. The lack of long term durability and resistance to calcification in heart valve prostheses comprised of polymeric or tissue leaflets has limited the universal acceptance and utility of these devices due to a recurrence of valvular stenosis and regurgitation which ultimately requires valve replacement.

SUMMARY OF THE INVENTION

The present invention is a multi-leaflet (usually trileaflet) biocompatible polymeric heart valve which, in all of its embodiments, simultaneously imitates the structure and dynamics of biological heart valves and avoids the promotion of calcification. Each of the valves of the various embodiments includes a plurality of flexible leaflets individually dip cast on a mandrel, which leaflets are then bonded with a bonding agent (adhesive) to the interior surfaces of a plurality of struts on a metal-reinforced prosthetic stent. The leaflets open and close in response to the pumping action of the heart and, due to the design of the leaflets, fatigue resistance of the heart valve is high. The leaflets and the polymeric components of the prosthetic stent are manufactured of biocompatible polymers, preferably polyurethane compositions as described hereinafter in the preferred embodiments.

A complete understanding of the invention will be obtained from the following description when taken in connection with the accompanying drawing figures wherein like reference characters identify like parts throughout.

BRIEF DESCRIPTION OF THE DRAWINGS

FIG. 15 is a section similar to FIG. 4 but showing dimensions of a typical heart valve according to the first embodiment of the invention;

FIG. 16 is a view in side elevation showing the dimensions of a typical strut reinforcing wire according to the first embodiment;

FIG. 17 is an end elevation taken in the direction XVII—XVII of FIG. 16;

FIG. 18 is a perspective view of a heart valve according to a second embodiment of the invention, in the closed position;

FIG. 30 is a plan view of the ring of the valve shown in FIG. 18 which forms part of the hood assembly;

FIG. 31 is a section on line XXXI—XXXI of FIG. 30;

FIG. 32 is an end elevation taken in the direction of the curved tip of the mandrel used in dip casting the leaflets of the heart valve shown in FIGS. 18 and 19;

FIGS. 33A, 33B, 33C and 33D are sections on lines XXXIIIA—XXXIIIA, XXXIIIB—XXXIIIB, XXXIIIC—XXXIIIC and XXXIIID—XXXIIID of FIG. 32;

FIGS. 25 through 31 show typical dimensions in inches for a heart valve in accordance with the second embodiment of the invention and FIGS. 33A through 33D show the significant dimensions in inches of a typical mandrel for dip casting leaflets in the practice of the second embodiment of the invention;

DESCRIPTION OF THE PREFERRED EMBODIMENTS

Figure 1:
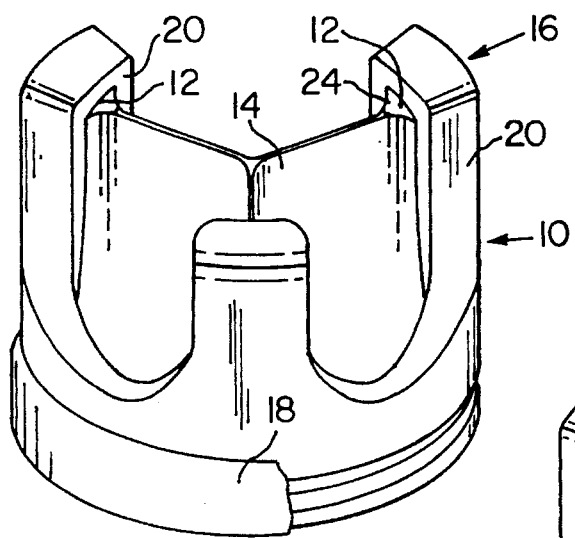
FIG. 1 is a perspective view of a heart valve according to a first embodiment of the invention in the closed position.
Figure 2:
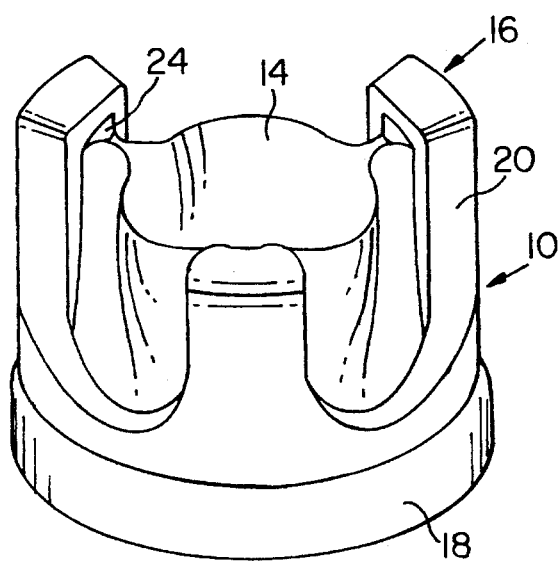
FIG. 2 is a perspective view of the valve of FIG. 1 in its open position.
Figure 3:
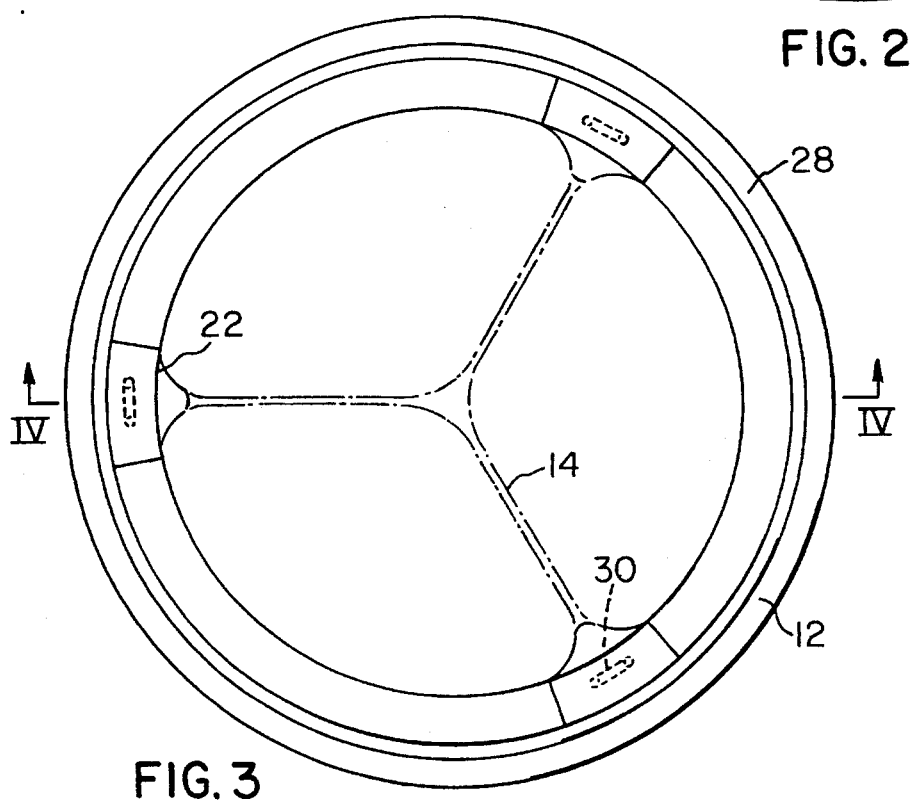
FIG. 3 is a plan view of the valve of FIG. 1.

Several embodiments of the present invention are described hereinafter. For clarity, they are described in the order in which they were developed and are shown in this same order in the drawings.

I. Description of the First Embodiment of the Invention

The apparatus shown in FIGS. 1 through 9 and 15 through 17 is a heart valve 10 in accordance with this invention including a metal-reinforced stent 12, flexible leaflets 14 connected to the stent, a hood 16 mounted on and secured to the stent and a suture ring 18 secured to the stent. The stent 12 has an annulus 19 (FIG. 4) from which struts 22 extend generally perpendicularly to the plane of the annulus. The struts 22 are enclosed in the projections 20 of the hood 16. Each projection 20 has a cavity 24 into which the corresponding strut 22 extends. The suture ring 18 is secured to the outer periphery of the annulus 19. The suture ring may be composed of polyester or other biocompatible suture ring material known in the art.

The stent 12 includes a metal frame 26 (FIGS. 7, 8, 9) having a ring 28 (FIGS. 5, 6) to which hairpin-shaped wire members 30 are secured generally perpendicularly to the plane of the ring. The frame 26 is embedded in a biocompatible polymer such as polyurethane 31, with the annulus 19 being formed of the ring 28 embedded in the polyurethane and the struts being formed of the members 30 embedded in the polyurethane. The hairpin-shaped members 30 endow the struts with flexibility, limiting the stress on the leaflets 14.

The ring 28 (FIGS. 5, 6, 7) is a circular strip which is machined out of a rod, typically of the MP35N alloy described below. A groove 32 is machined in the outer periphery of the ring 28. The ring 28 also has notches 34 in opposite surfaces around its periphery. Slots 36 (FIG. 5) are machined along the outer periphery of the ring 28, typically at 15° intervals. A string 38 (FIG. 7), typically of polyester suture material of 0.010-inch diameter, is successively passed through the slots 36 and wound around the ring 28. The string 38 enhances the ability of the polyurethane portion of the stent 12 to adhere to the ring. The string becomes impregnated with the polyurethane and thus embedded in the polyurethane, so that the adhesion of the ring to the polyurethane is enhanced. The string may be pre-impregnated if desired to achieve the same result.

The ring 28 also has pairs of holes 40 (FIG. 5) symmetrically positioned about its center, typically spaced at 120° positions around its periphery. The ends of hairpin-shaped wires 30 are inserted in these holes and welded. Typically, both the ring 28 and the wires 30 are composed of MP35N alloy, an alloy having a composition of Cobalt 35%, Nickel 35%, Chromium 20% and Molybdenum 10%. The stent can alternatively be stamped out of sheet metal of the same composition. The wire for the hairpin-shaped wires 30 is available through the Fort Wayne Wire Co., of Fort Wayne, Ind., and the MP35N metal for the wires or the ring may be bought from Latrobe Steel Company of Latrobe, Pa. However, a biocompatible material with properties similar to MP35N may also be used.

For simplicity, the ensuing descriptions refer to polyurethane but any biocompatible polymer may be substituted for the polyurethane. This applies to all embodiments.

Figure 11:
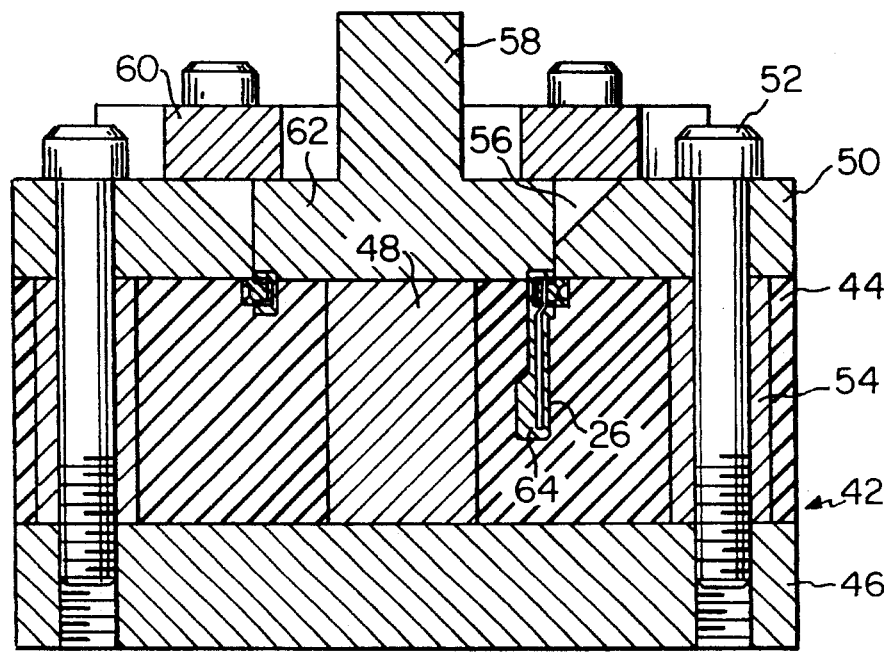
FIG. 11 is a view along line XI—XI of FIG. 10, but with bolts unsectioned for clarity.

Referring now to FIG. 11, the frame 26 is embedded in polyurethane in a mold assembly 42 including an annular mold 44 of rubber or other yieldable material. The mold assembly includes a base 46, a central cylindrical member 48 and a ring 50. The mold 44 is mounted in a space defined between the base 46, the cylindrical member 48 and the ring 50 and is secured by bolts 52 which pass through sleeves 54 near the outer periphery of the mold 44 and are screwed into a thread in the base 46. The inner periphery of the ring 50 is beveled, providing a space 56 for escape of the polyurethane molding compound which forms the stent. A closure 58 having a generally inverted T longitudinal section extends over the top of the cylinder 48 and up to the top of the mold and is secured by another ring 60 extending over part of ring 50 and part of cross member 62 of closure 58. The ring 60 is bolted to ring 50. The mold 44 has a cavity 64. The frame 26 is mounted within the cavity 64 and the components which form the polyurethane embedding or coating in liquid phase are poured into the cavity and then the mold is evacuated to remove bubbles. One supplier of this material is Thermedics of Woburn, Mass. in a kit under the name Tecoflex 2-80. But any biocompatible polymer liquid molding compound may be used. The frame 26 is suspended with the end of the ring 28, which includes the groove 32 extending into a cavity in the cross member 62 of the closure 58. Any polyether polyurethane which accumulates on the end of the ring 28 is removed after the molding.

Figure 12:
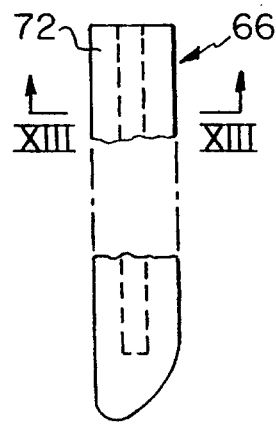
FIG. 12 is a side elevation of the mandrel used in dip casting the flexible leaflets of the heart valve of FIG. 1.
Figure 13:
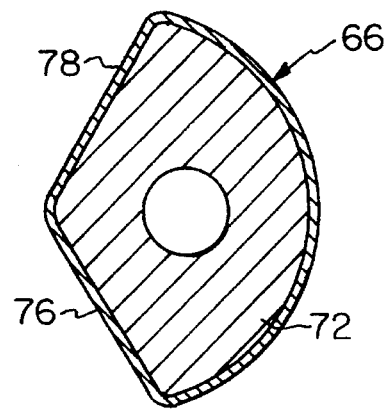
FIG. 13 is a view along line XIII—XIII of FIG. 12.

The valve leaflets 14 are formed by dip casting on a ceramic metallic or polymer mandrel 66 (FIGS. 12, 13). Laterally, the mandrel 66 has a contour which matches the inner edge surfaces 68 of the struts 22 and the contour 70 of the surfaces where the struts 22 merge into the annulus 26.

The following steps exemplify the dip casting process. First, a solvent composed of two parts of N,N-dimethylacetamide (DMA) and one part of tetrahydrofuran (THF) is prepared. The mandrel is insoluble in this solution. An adequate quantity, typically 10% by weight of the solution, of polyurethane is dissolved in this solvent and the solution is filtered. The mandrel is repeatedly dipped into the solution and the solvent is removed by drying. During drying, the more volatile THF is evaporated first and then the lower volatility DMA is evaporated. During drying, the more volatile THF evaporates quickly causing a rapid rise in the viscosity of the dipping Solution, preventing excessive drainage of the coating. The lower volatility DMA evaporates slowly, producing a smooth and uniform thin leaflet. The dipping and drying continues until a uniform coating 72 (FIG. 13) of the desired thickness, typically 0.005-inch, is produced on the surface of the mandrel. Because of the components of the solvent and the sequence of their drying, the coating 72 is smooth.

Figure 14:
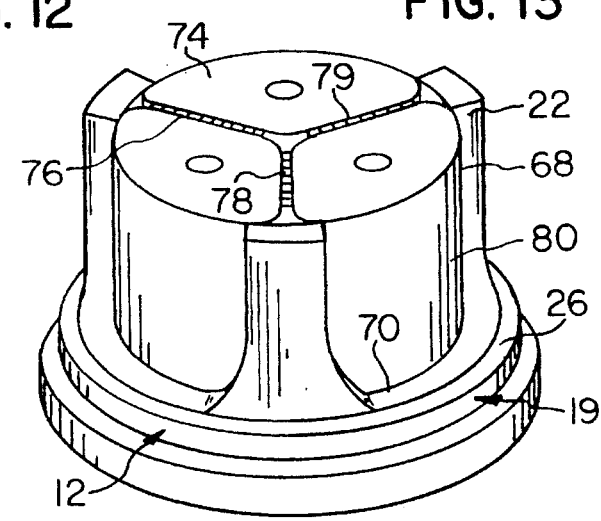
FIG. 14 is a perspective view of the heart valve according to FIG. 1 prior to removal of the mandrels.
Figure 19:
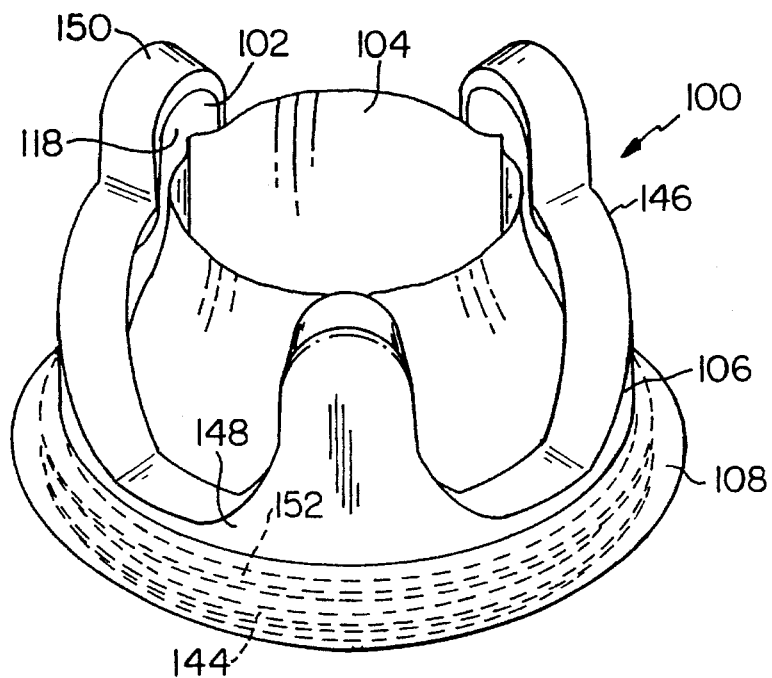
FIG. 19 is a perspective view of the heart valve of FIG. 18, in the open position.
Figure 20:
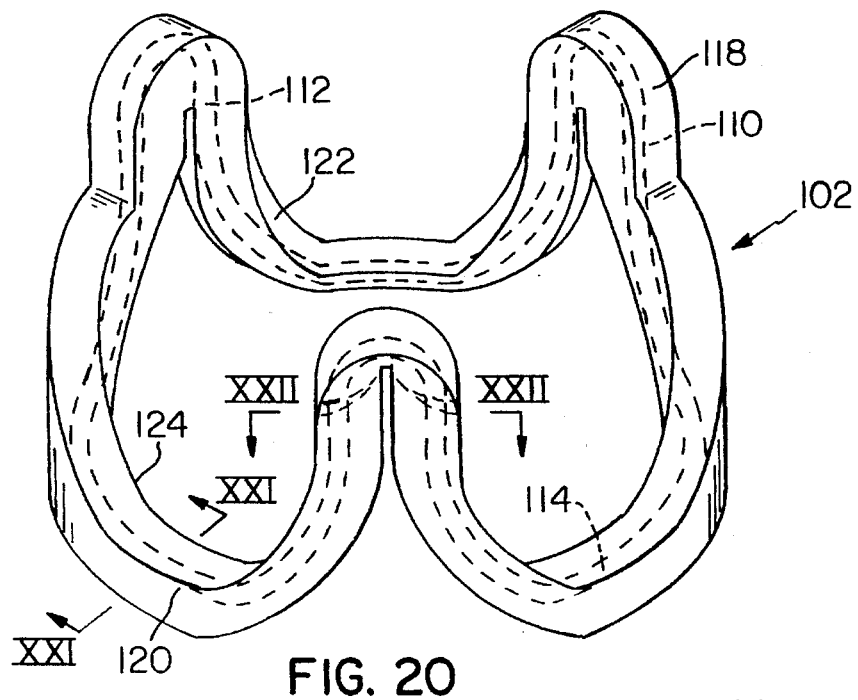
FIG. 20 is a perspective view of the stent of the heart valve shown in FIGS. 18 and 19.
Figure 21:
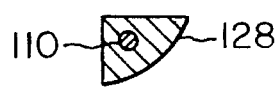
FIG. 21 is a section on line XXI—XXI of FIG. 20.
Figure 22:
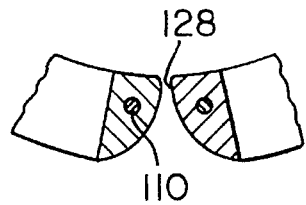
FIG. 22 is a section on line XXII—XXII of FIG. 20.
Figure 23:
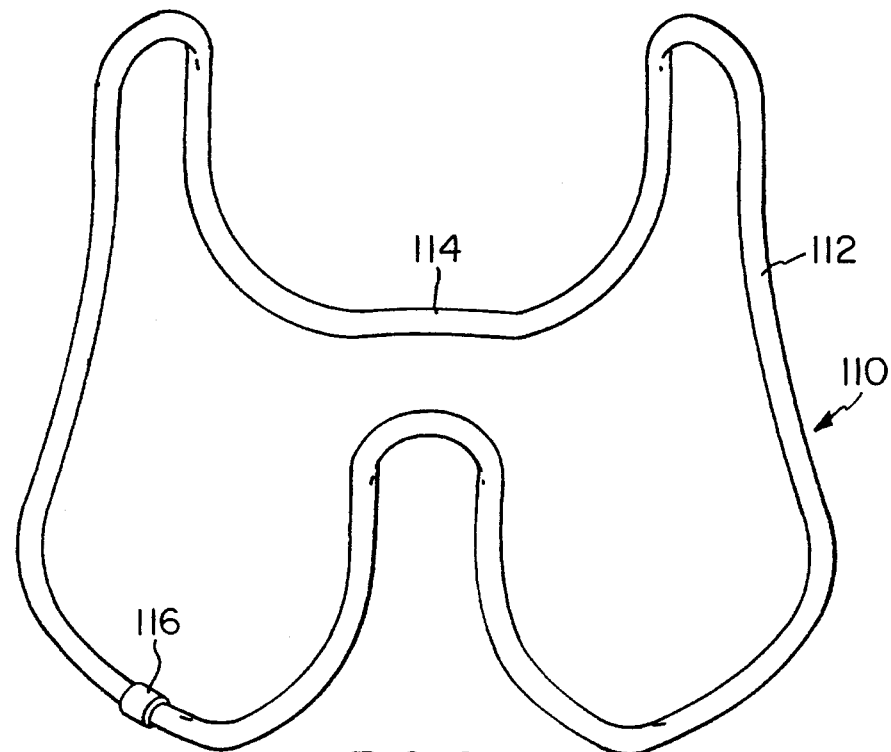
FIG. 23 is a perspective view of the wire embedded in the stent shown in FIGS. 20 through 22.

After initial formation of the layer 72, the layer is subjected to preliminary stress relieving in an atmosphere of DMA vapor at 50° C. for about 60 to 90 minutes, after which the coated mandrel is cut to size to form the unit 74 shown in FIG. 14. Three units 74 (or any other number equal to the number of struts 22) are produced. The edges of the units 74 are dipped in DMA or another suitable solvent and dried to round off any sharp edges produced by the cutting.

With the aid of a fixture, the units 74 are placed between the struts 22 of the stent 12. Each unit 74 seats along the edge 68 and the contour 70 between two successive struts 22 with opposite sides 76 and 78 abutting along their planes to form converging joints of the planes. Where the units seat they are bonded with an adhesive. The adhesive typically consists of a solution of about 17–25% of polyurethane dissolved in DMA, and the assembly is held in the fixture until the adhesive is cured.

After curing, the assembly is treated in an atmosphere of DMA at 50° C. for about 60 to 90 minutes to relieve stress in the layers 76. After this stress relieving treatment, the cut-off parts 74 of the mandrel(s) 66 are removed, leaving in place the struts 22 with their adjacent flexible leaflets 14 secured in place.

The hood 16 is composed of polyurethane and is formed in a mold similar to the mold 44 (FIG. 11). The hood mold is provided with projections to form the cavities 24. The hood 16 is mounted on the stent 12 with the struts 22 within the cavities. The inner surface of each cavity is secured to the outer surface of the corresponding Strut by the same adhesive as described above for bonding leaflets to the stent. The hood engages the top of the annulus 26 and is secured to the annulus by the Same adhesive. The purpose of the hood 16 is to cover the rough edges of the leaflets where the leaflets are cut and have been bonded to the top of the stent. The projections 20 of the hood 16 overlap the edges of the leaflets. The groove in the end of the ring 28 extends outwardly of the hood. The suture ring 18, which is composed of implantable polyester cloth, is secured in the groove 32.

Figure 4:
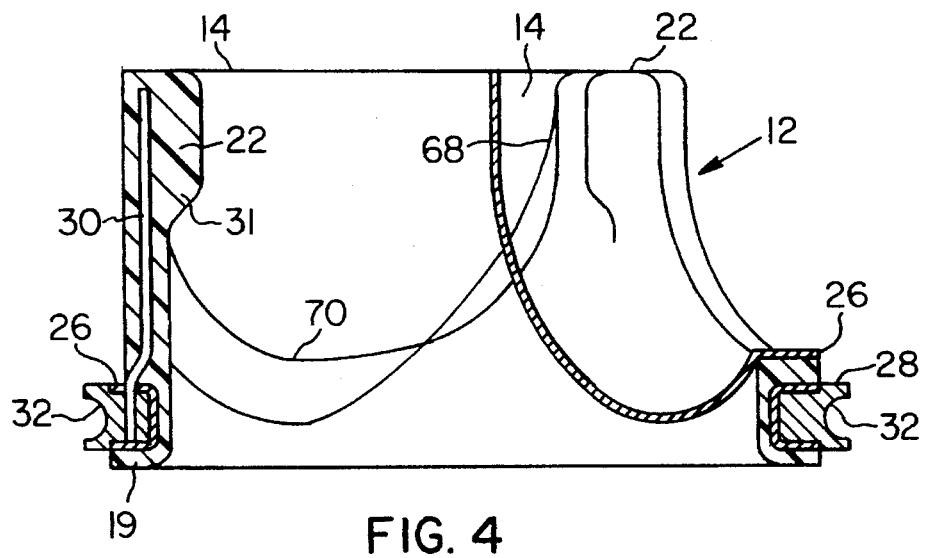
FIG. 4 is a section on line IV—IV of FIG. 3.
Figure 4A:
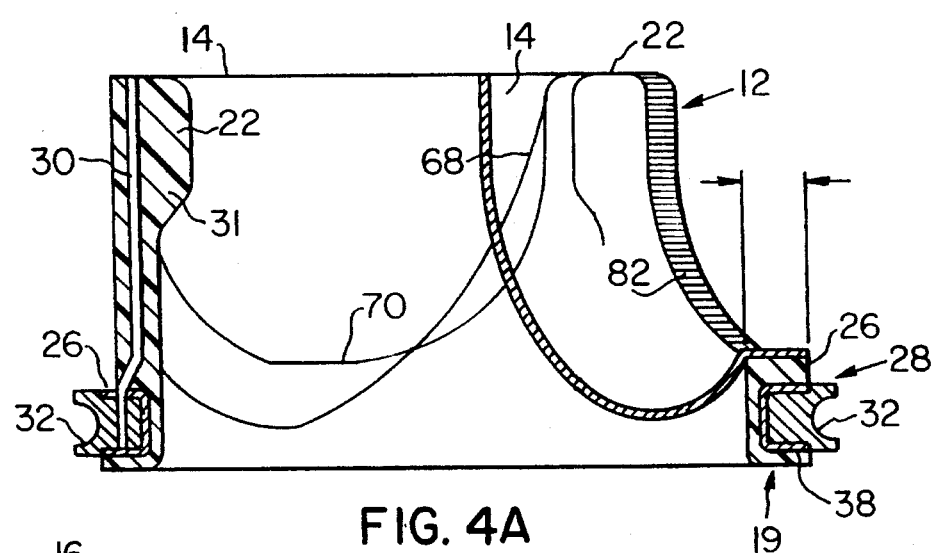
FIGS. 4A, 4B, 4C are views similar to FIG. 4 but show the procedure stage-by-stage followed in integrating the stent, the leaflets, the hood and the suture ring into a heart valve according to the first embodiment.
Figure 4B:
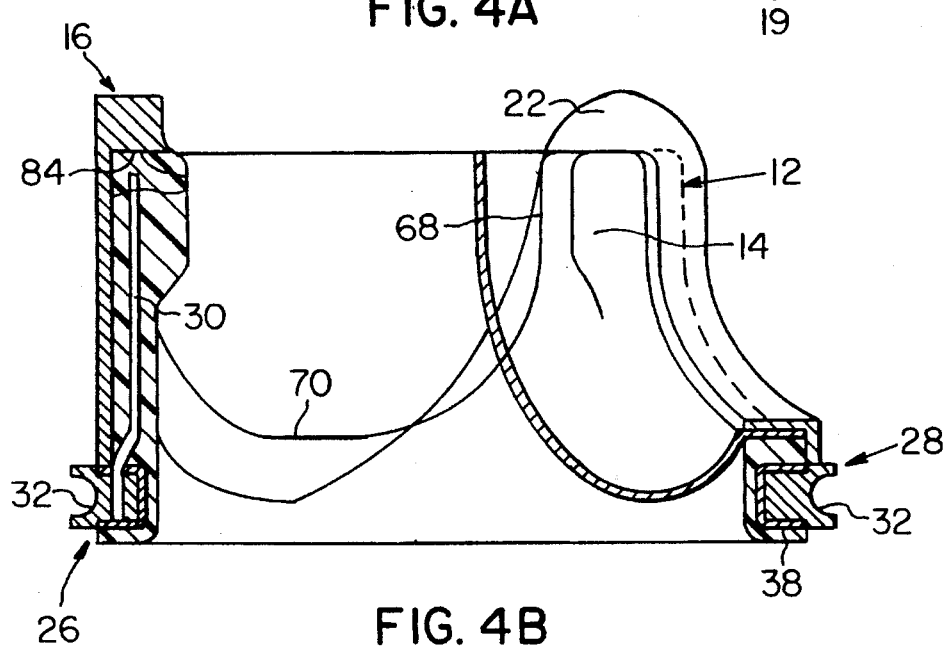
Figure 4C:
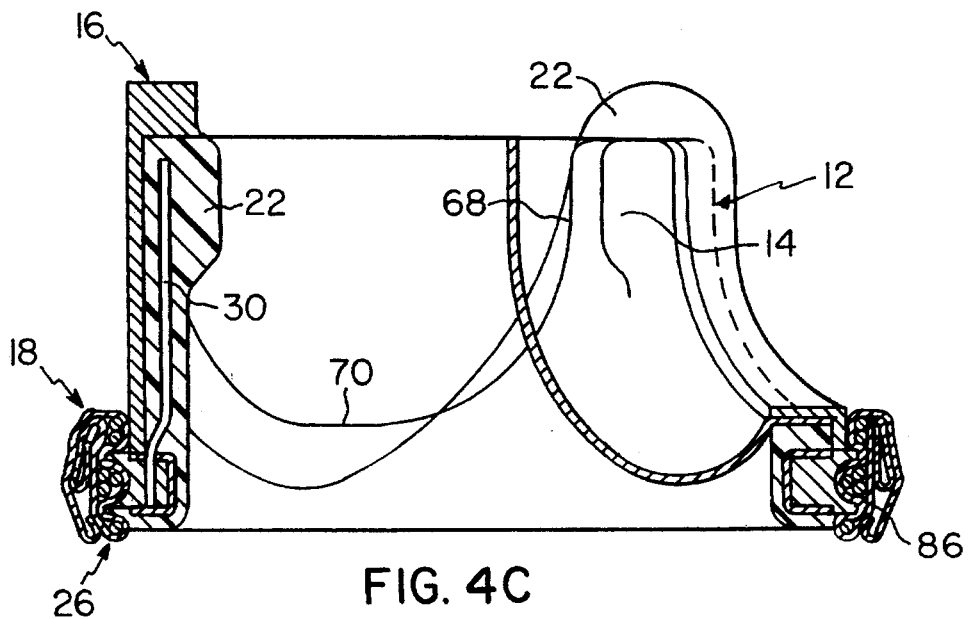
Figure 5:
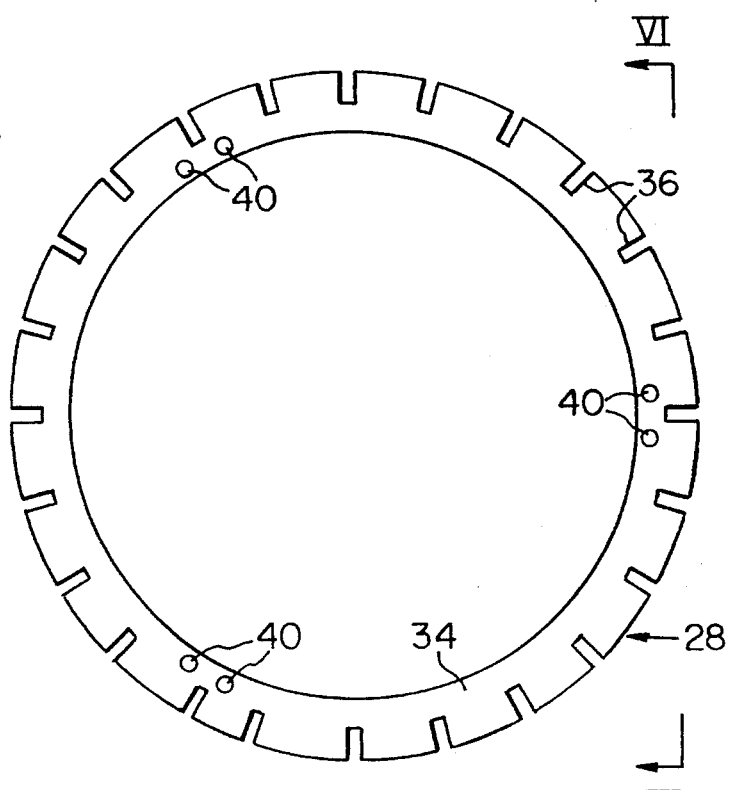
FIG. 5 is a plan view of a ring component of the valve of FIG. 1.
Figure 6:
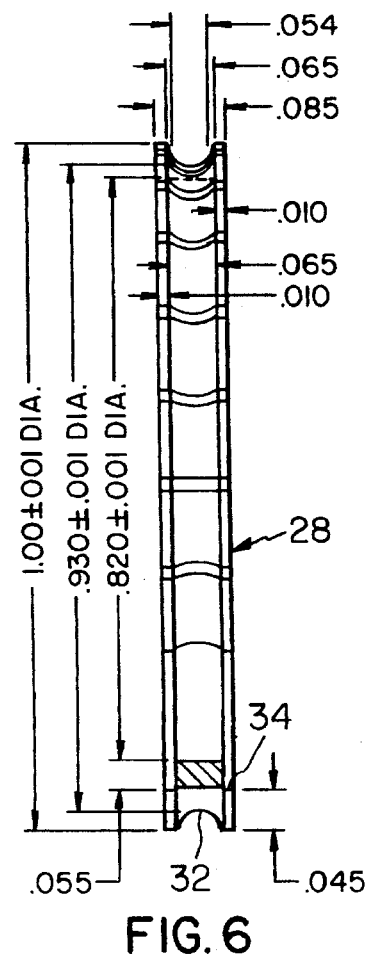
FIG. 6 is a side elevation in the direction VI—VI of FIG. 5.
Figure 7:
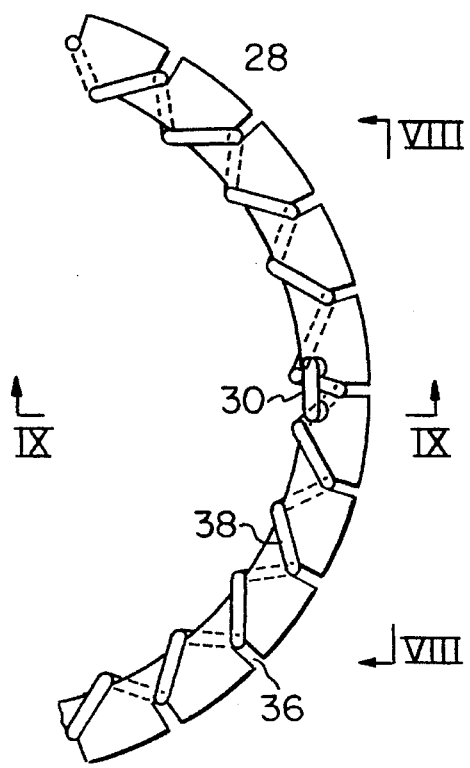
FIG. 7 is a fragmental view of the ring of FIG. 5 with string wound therearound.
Figure 8:
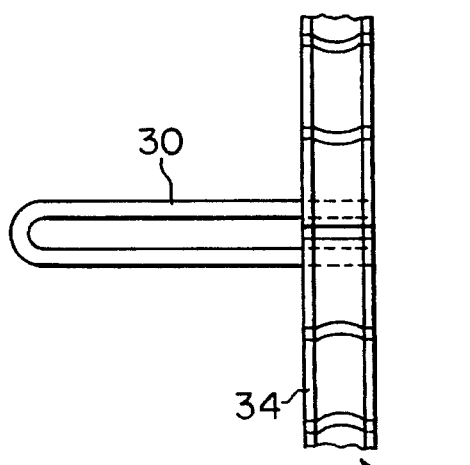
FIG. 8 is a view along lines VIII—VIII of FIG. 7.
Figure 9:
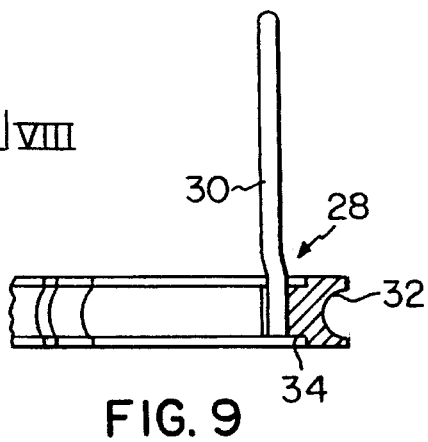
FIG. 9 is a view along lines IX—IX of FIG. 7.
Figure 10:
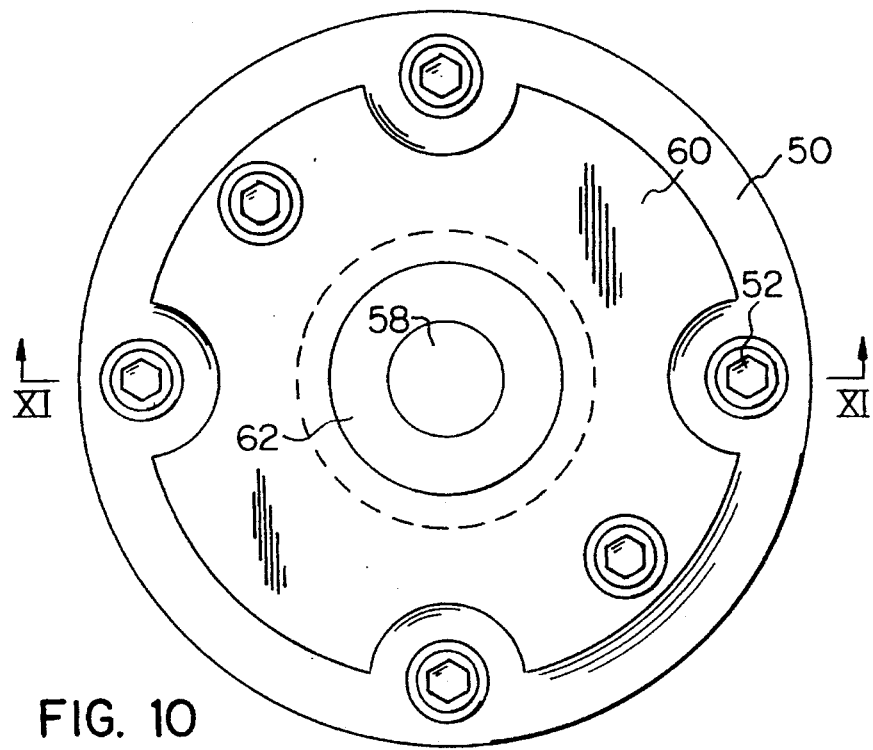
FIG. 10 is a plan view of the mold in which the stent is formed.

FIG. 4A shows the first stages in the procedure of producing the heart valve 10. This step follows the completion of the stent 12. Each leaf 14 is adhered to the stent 12 along a stippled area 82 of each strut and the contour 70. In the next stage shown in FIG. 4B, the hood 16 is mounted upon the stent 12 and adhered to the stent in regions 84 along the tops and sides of the struts 12. The lower edge of the hood 16 extends only to the top of the ring 28. The final stage is shown in FIG. 4C. The suture ring 18, which is composed of an implantable polyester cloth, is secured to the ring with implantable polyester suture thread 86.

A valve, in accordance with this invention, whose stent has an inner diameter of 25 mm, was successfully implanted in a dog at the Allegheny General Hospital Animal Research Laboratory, in Pittsburgh, Pa., and its performance was very close to that of the natural valve which it replaced. The pressure drop across the valve was low, its dynamic response was excellent, and the hemolytic effect on the dog's blood was minimal. The dog recovered from the operation and had returned to normal behavior prior to expiring 24 hours after the surgery due to heart arrhythmia induced by the surgery. Another 25 mm valve was implanted in a dog, with excellent hemodynamic and dynamic pressure responses. The dog recovered successfully, but after six days died due to a perivalvular leak through a tear which had developed at the site of the sewing ring. The heart valve implanted in the dogs did not include a hood 16. The absence of such a hood does not affect the mechanical function of the valve. The function of this hood is to cover the roughcut edges of the leaflets and present a smooth surface to the blood flow which minimizes thrombus formation.

A valve according to the above-described embodiment, which had an inner diameter of 19 mm, was tested for fatigue failure. The valves were cycled in an accelerated fatigue test machine for 600 million cycles which corresponds to 15 years of normal human heart beats without failure.

II. Description of the Second Embodiment of the Invention

This application also incorporates a second embodiment, which is a variation on the first embodiment described above.

The heart valve according to the first embodiment, which itself reduces unwanted backflow of blood through the leaflets, can be made additionally to reduce unwanted backflow of blood through the leaflets in this second embodiment of the present invention. In the first embodiment, the openings in the seams between adjacent leaflets and in the region of convergence in the closed position arise from the fact that its leaflets are joined internally of the stent to its struts. A pair of adjacent leaflets of the heart valve according to the first embodiment are joined to the nose of the strut at spaced positions on the nose and are thus separated from each other or spread at these joints. The gap between adjacent leaflets at the joints can to an extent be reduced by deflecting the leaflets near the joints, but this expedient produces relatively sharp edges in the regions of the joint and concentration of stress.

In the heart valve according to the second embodiment, the stent on which the leaflets are mounted is formed of a plurality of metal-reinforced branches arrayed end-to-end in a continuous closed curve configuration, specifically a circular configuration. In accordance with this invention, each leaf is passed through the joints between ends of adjacent branches and is adhered to the outer surface of a branch. Adjacent leaflets brought through a common joint converge between branches to contact each other. The outer surfaces of the branches are curved and smooth with each leaf having the shape of a curved surface which merges into an angle. The leaflets are mounted with their angles converging and with the end of each leaf adhered to the outer surfaces of an associated branch. For effective connection to its associated branch, each leaf is provided with a curved end member which has the same curvature as the outer surface to which it is adhered. This structure has an advantage in that there are no sharp edges in the joint between each leaf and the branch to which it is adhered. In addition, assembly of the leaflets and the stent is facilitated and costs of assembly are materially reduced. The leaflets are bonded to the stent in a non-stressed condition and all glue joints are under either shear stress or compression stress when in the closed condition.

An important feature of the second embodiment is therefore the structure of the stent. The stent is formed of a continuous wire frame embedded in biocompatible polymeric material. The frame includes U-shaped members joined by members interconnecting adjacent legs of the U-shaped members. The U-shaped members are also referred to as "struts." The stent which is produced by embedding the frame includes U-shaped struts formed by embedding the U-shaped wire members in the biocompatible polymeric material. Adjacent pairs of legs of adjacent struts are joined by a curved interconnecting member. A branch of a stent is defined as the part of a stent including adjacent legs of successive U-shaped members and the curved member interconnecting these adjacent legs. Each leaf is adhered to the external surfaces of its associated legs of the adjacent struts and of the external surface of the curved member interconnecting these associated legs., i.e., to the external surface of a branch of the strut.

Although the above summarizes the second embodiment of the invention, the second embodiment is best understood with reference to the applicable FIGS. 18–33 of the drawings.

FIGS. 8 through 31 show a heart valve 100 including a stent 102, to which leaflets 104 are adhered, a hood assembly 106 and a suture ring 108.

The stent 102 (FIGS. 20–23) is composed of wire-reinforced biocompatible polymeric material, typically polyurethane. As reinforced, the stent is resilient, and as such dissipates the stresses the leaflets 104 are subjected to as they flex between the closed and open positions. The wire reinforcement is a continuous wire 110, including a plurality of U-shaped members 112 joined by interconnecting members 114. Typically, the wire is composed of the corrosion-resistant alloy MP35N as described in previous embodiments. The wire 110 is formed into the U-shaped configuration from a straight wire and joined at the ends by a coupling 116. With the wire 110 embedded in biocompatible material, the stent 102 has a shape corresponding to the shape of the wire. The stent 102 has U-shaped members 118 (FIGS. 20, 26) joined by, or smoothly emerging into, interconnecting members 120. Adjacent legs of successive U-shaped members 118 are joined by an interconnecting member 120. The U-shaped members 118 essentially constitute struts. The stent may be regarded as containing a plurality of branches 122, 124, 126 (FIGS. 20, 26) arrayed in a circular configuration. Each branch includes adjacent legs of successive U-shaped members 118 and the interconnecting member 120. The stent 102 is formed in a mold about the wire 110. The walls of the cavity of the mold are shaped to endow the outer surfaces of the branches 122, 124, 126 with a curved surface 128 (FIGS. 21, 22, 24, 25, 27).

Figure 24:
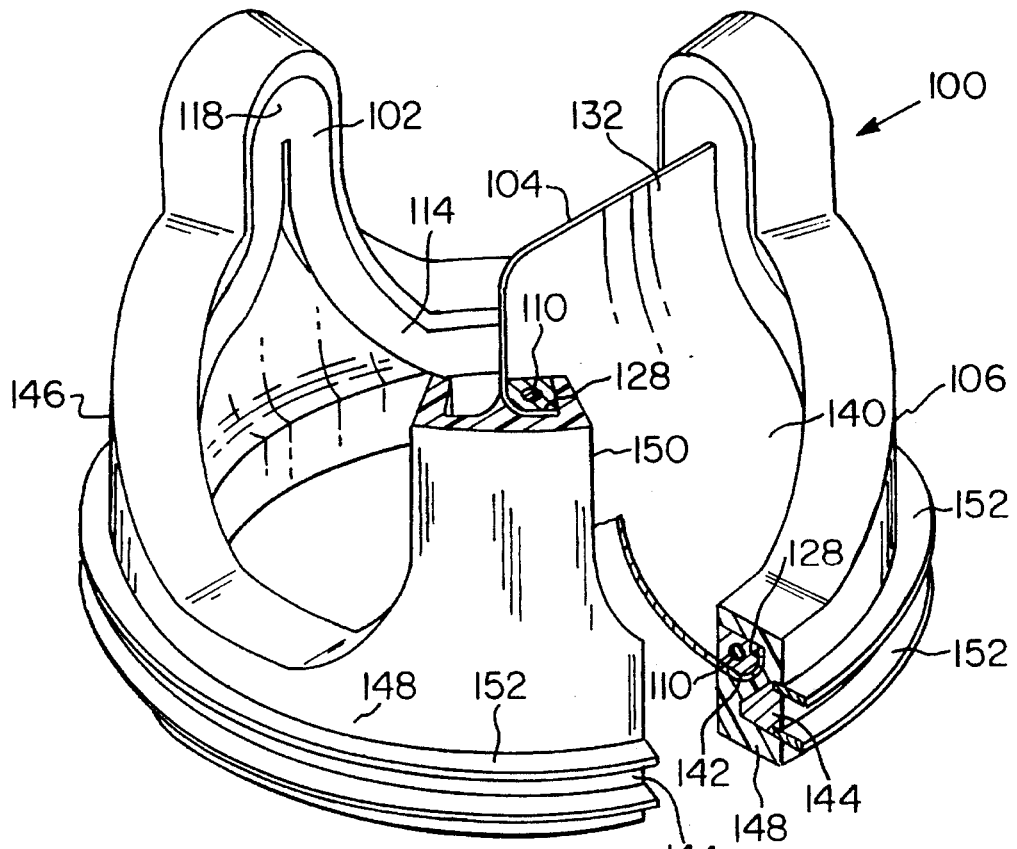
FIG. 24 is a perspective view, partly in section with parts broken away, showing the manner in which the leaflets are secured to the stent in the valve shown in FIGS. 18 and 19.

Each leaf 104 is shaped to have a curved surface 132 which merges smoothly into an angular surface 134 (FIGS. 18, 24). Each leaf 104 is formed by dip casting on a ceramic, metallic or polymeric mandrel 136 as shown in FIGS. 32, 33A, 33B, 33C, and 33D having typical dimensions as shown. Each leaf is formed essentially by the same dip casting method as disclosed above for the first embodiment of the present heart valve. The mandrel 136 is repeatedly dipped into a solution of polyurethane in a solvent consisting typically of but not limited to two parts N,N-dimethylacetamide (DMA) and one part of tetrahydrofuran (THF). The coating on the mandrel 136 is oven dried, typically at 50° C., after each dipping. The dipping is repeated until the coating has the desired thickness. The thickness of the leaflet material is typically, but not limited to, the range of 0.0050 inch to 0.0070 inch in thickness with a nominal thickness of 0.0055 inch.

Figure 26:
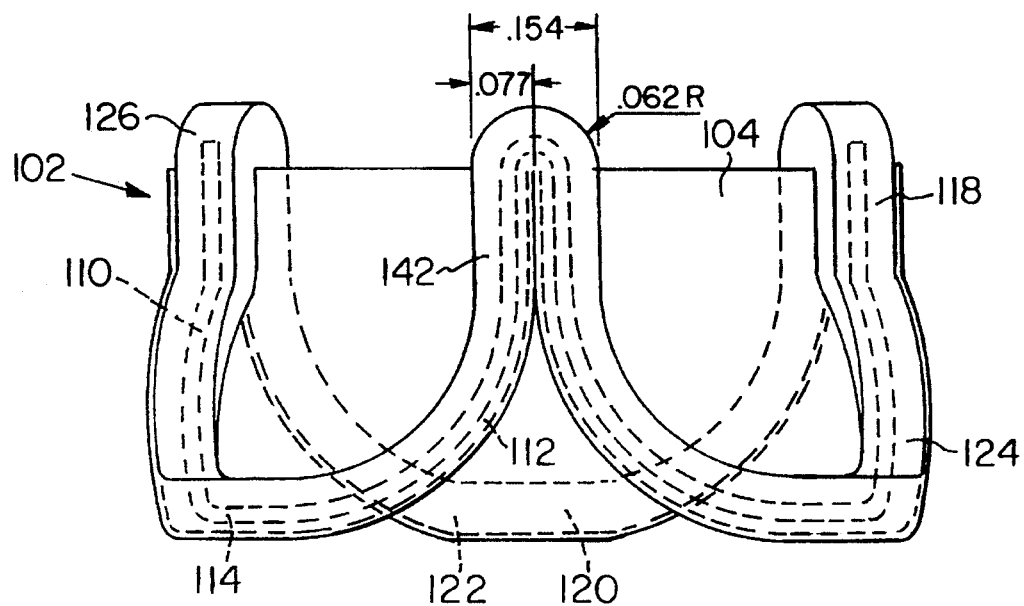
FIG. 26 is a side elevation taken in the direction XXVI—XXVI of FIG. 25.
Figure 27:
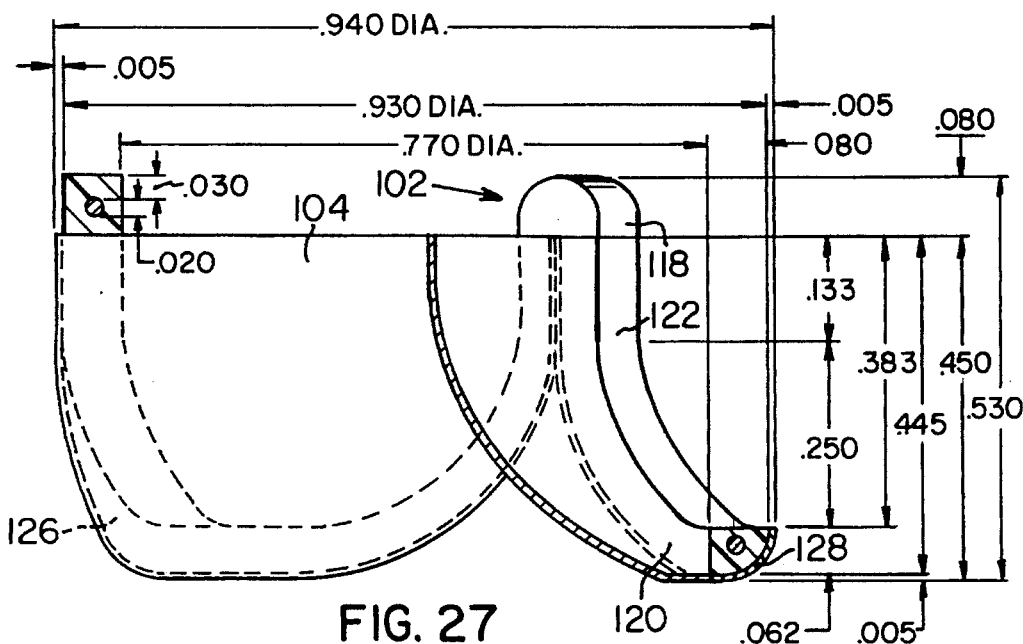
FIG. 27 is a section on line XXVII—XXVII of FIG. 25.

The mandrel 136 has rounded corners 138. The rounded corners 138 have the same radius as the outer curved surfaces 128 of the branches 122, 124, 126 (FIG. 26). After the coating on the mandrel 136 having the desired thickness is dried, the coating is cut in a plane perpendicular to its major axis 140. The leaf formed has a curved member 142 (FIG. 24) of the same radius as the outer curved surfaces 128 of the branches 122, 124, 126 along its outer rim.

An adhesive, typically about 15–25% of polyurethane in DMA, is applied to the outer surface 128 of each branch 122, 124, 126, each in its turn, of the stent 102 and the associated leaf 104 is bonded to the branch by adhering the curved member 142 to the surface. This operation is carried out in a fixture and the members 142 are held in engagement with the surface 128 until the adhesive dries. The assembly need not be stress relieved because there is no bend at the joint between each leaf and the stent and therefore no stress will be developed.

Figure 25:
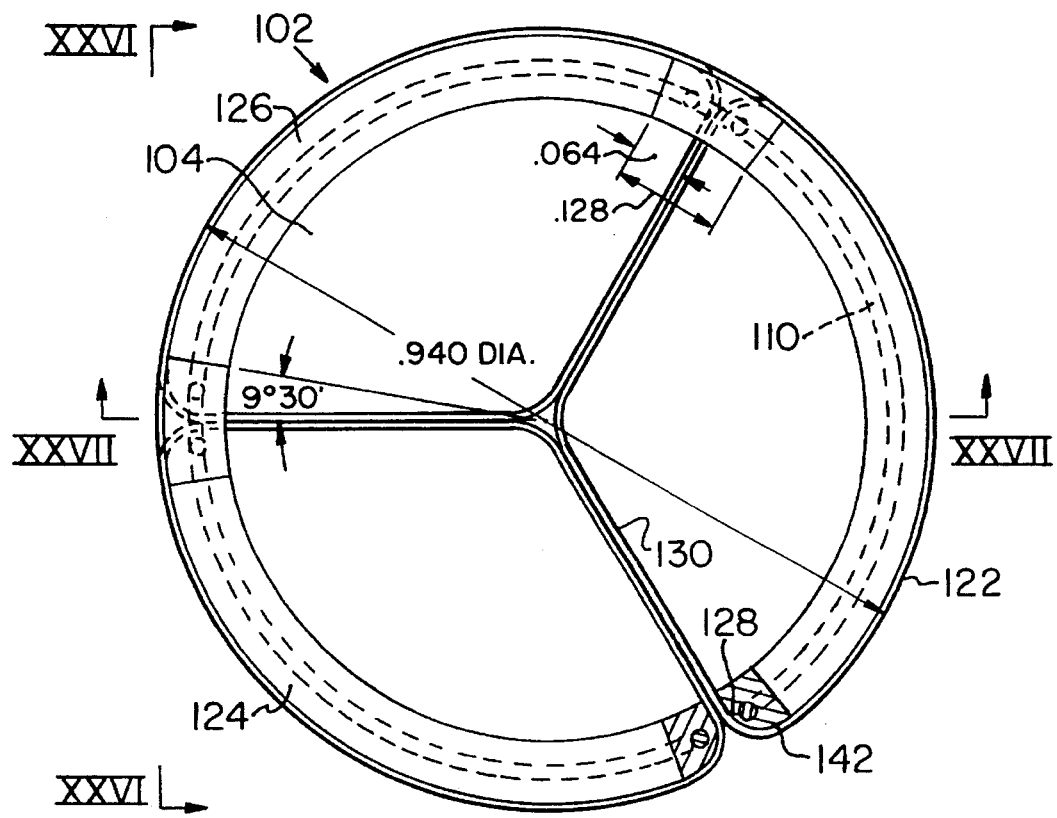
FIG. 25 is a plan view partly in section showing the assembly of the stent and the leaflets of a valve according to this invention.

As can be seen from FIGS. 24 and 25, adjacent leaflets 104 can be secured so that the contiguous sides 130 (FIGS. 25, 28) of their curved surfaces 132 are substantially in contact. Backflow of blood through the valve 100 in the closed position is minimized. The connection of each leaf 104 to the associated strut does not require the leaflet to be bent, thus there is no concentration of stress as each leaf flexes.

Figure 28:
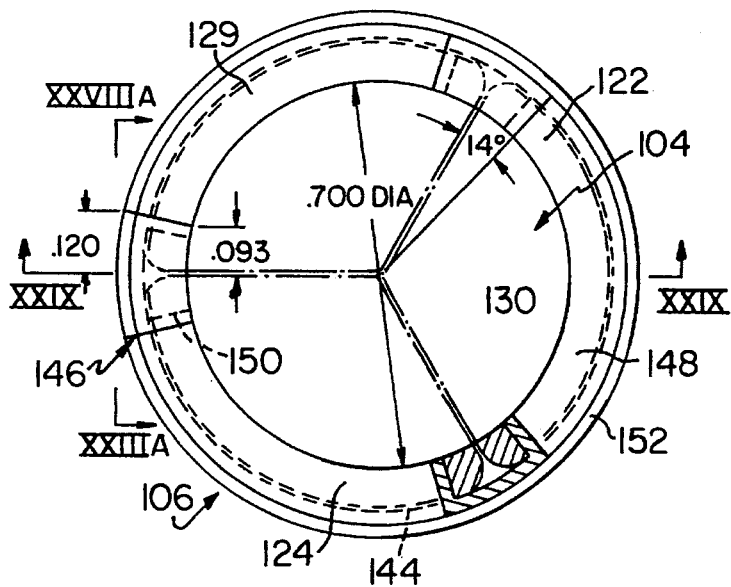
FIG. 28 is a plan view, partly in section (FIG. 28A), of the valve shown in FIGS. 18 and 19 with the suture ring removed.
Figure 28A:
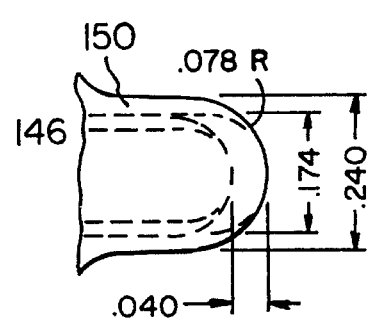

The hood assembly 106 (FIGS. 28, 28A, 29), which forms part of the stent 102, includes a ring 144, typically of a titanium alloy, and a molded polymeric hood 146. The hood 146 has an annulus 148 from which projections 150 extend. The tips of the projections 150 are rounded to avoid sharp corners and thus to improve biocompatibility. The ring 144 is embedded in the annulus. The ring 144 has short flanges 152 defining a circumferential slot.

Figure 29:
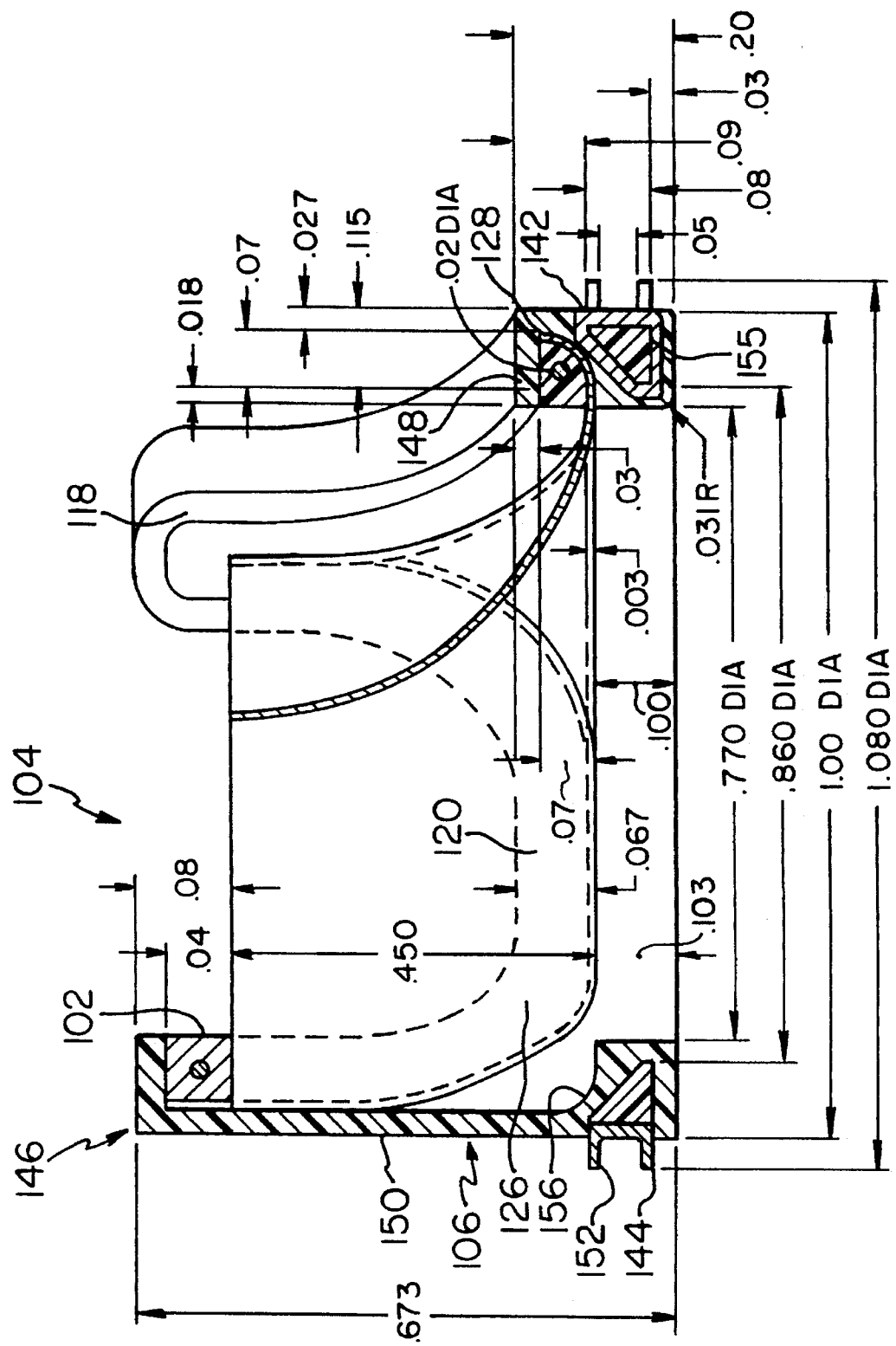
FIG. 29 is a section on line XXIX—XXIX of FIG. 28.

The flanges 152 of the ring 144 have slots 154 (FIG. 30), typically at 15° intervals, around the periphery. A string 155, typically of Dacron® composition, is passed through the slots in succession and wrapped around the body of ring 144. The embedding of the ring 144 and string 155 in biocompatible polymeric material of the hood 146 is effected in a mold as described for the first embodiment of the invention. As shown in FIGS. 24 and 29, only the body of the ring 144 is embedded; the flanges 152 are not embedded.

The projections 150 of the hood 146 enclose and are adhered to the U-shaped members 118 or struts of the stent 102 (see FIG. 24). The internal surfaces 156 of the projections having a curvature such as to seat the members 142 which are adhered to the surfaces 128 of the stent (FIG. 29).

The suture ring 108 (see FIG. 19) is composed of implantable polyester cloth and is mounted on and tied to the flanges 152, penetrating into the slot between the flanges. The heart valve 100 is sutured in the desired position in the heart by means of this suture ring 108. The leaflets 104 are flexed between open and closed positions by the variation in pressure in the heart. Because contiguous leaflets are laterally in engagement with each other, backflow of blood is minimized.

III. Description of the Third Embodiment of the Invention

Figure 34:
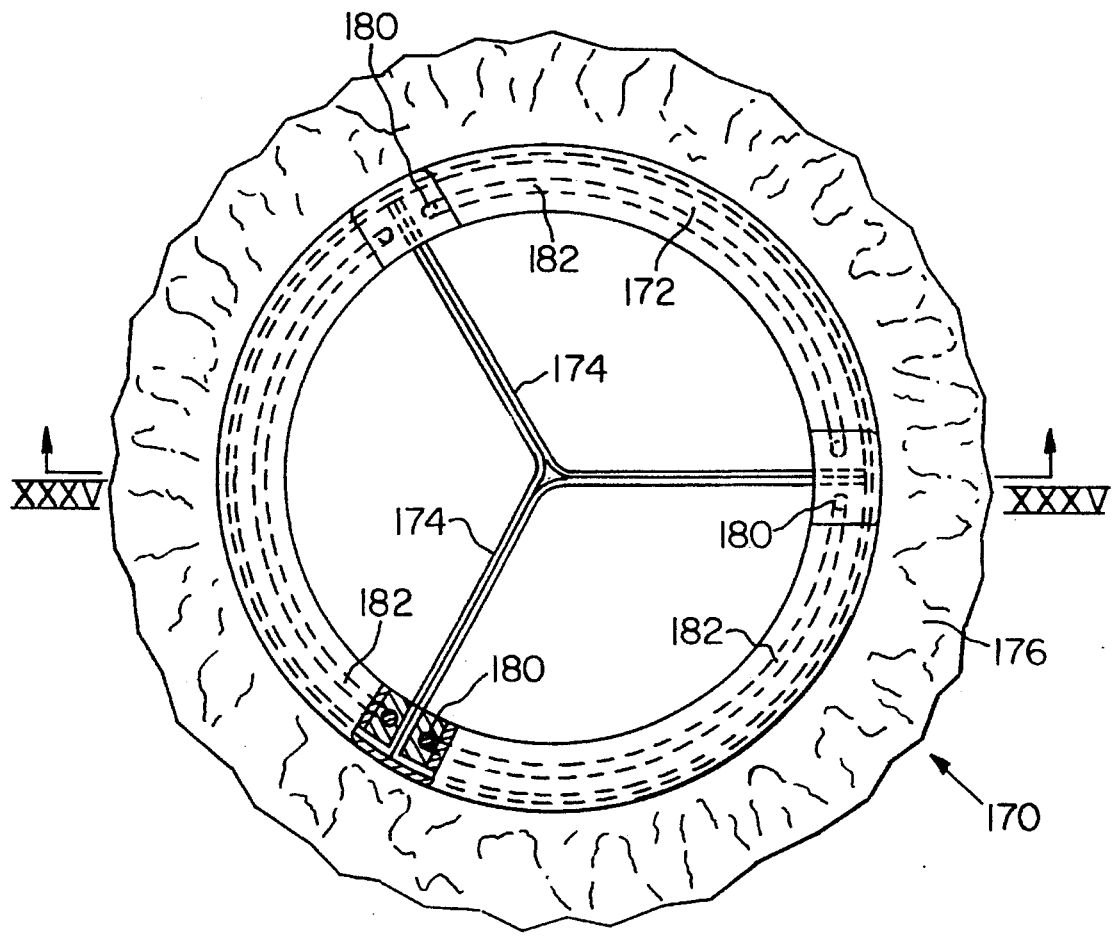
FIG. 34 is a plan view of a heart valve according to a third embodiment of the invention having only slight design variation from the heart valve of the second embodiment.
Figure 35:
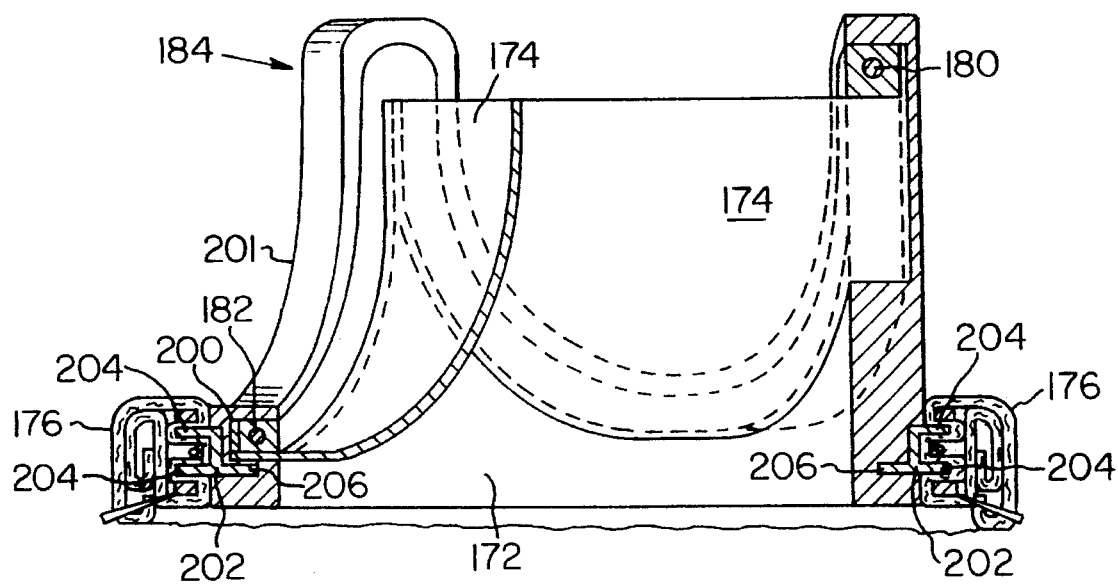
FIG. 35 is a section on line XXXV—XXXV of FIG. 34.

FIG. 34 is a plan view of a third embodiment of the present heart valve, having only slight design variation from the heart valve of the second embodiment. FIG. 35 is a section along lines XXXV—XXXV of FIG. 34. The design of the third embodiment is so similar to the second embodiment that it is more clear to describe the differences than to reiterate the similarities. The same materials are used as are used in the first and second embodiments, and apart from explained differences the valve embodiments should be assumed to be the same.

The third embodiment of the present heart valve 170 includes the same basic stent 172, leaflets 174 and suture ring 176 as does the second embodiment of the invention. Also the same are the plurality of U-shaped members of wire 180, the interconnecting members 182, and the U-shaped members 184 of the stent 172. The structural differences between the second and third embodiments are apparent from comparison of FIGS. 24 and 35. In FIG. 24, the annulus of hood 148 can be seen as containing both the ring 144, which ring in section has a generally triangular body with two flanges 152 appending therefrom, and the branches—most notably the outer surface of branch 128. In FIG. 35, the ring 202 does not have a triangular body but instead has a flat internal ring flange 206, in addition to the two external ring flanges 204. The flat internal ring flange 206 has holes—typically 0.020 inches in diameter—drilled at approximately 15° intervals throughout, and thus adheres even more securely within the polymer portion of the hood assembly 201, due to its shape (FIG. 35) and due to the mechanical anchoring provided by the perforated flange, than does the triangular body of the ring 144 within the annulus of hood 148 (FIG. 24). Also in FIG. 35, it is apparent that the third embodiment has a rectangular outer surface of branch 194, instead of the curved outer surface of branch 128 (FIG. 24). The corresponding rectangular member of leaf 200 (FIG. 35) substitutes for the curved member of leaf 142 (FIG. 24), with the angled bonding of the rectangular member of leaf 200 within the hood assembly 201 being more secure and less likely to pull free than is the curved member of leaf 142 after it is bonded into place. Easier, consistent and repeatable assembly is also facilitated. Although the rectangular member of leaf 200 (FIG. 35) and the curved member of leaf 142 (FIG. 24) can be the same structure when cast, taking on their different structures only after they are bonded into place, preferably the leaflets are cast on mandrels shaped to match the shape of the stent.

IV. Description of the Fourth Embodiment of the Invention

Figure 36:
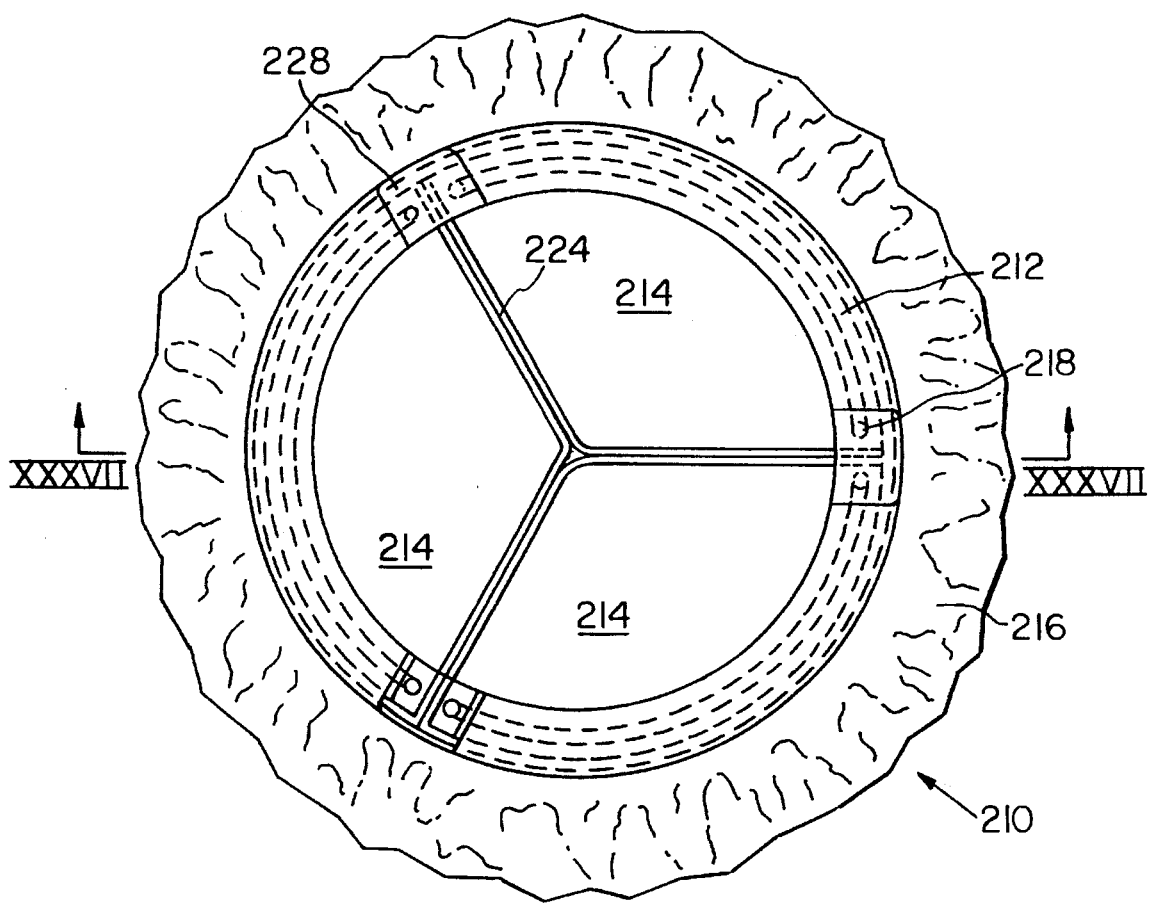
FIG. 36 is a plan view of a heart valve according to a fourth embodiment of the invention.
Figure 37:
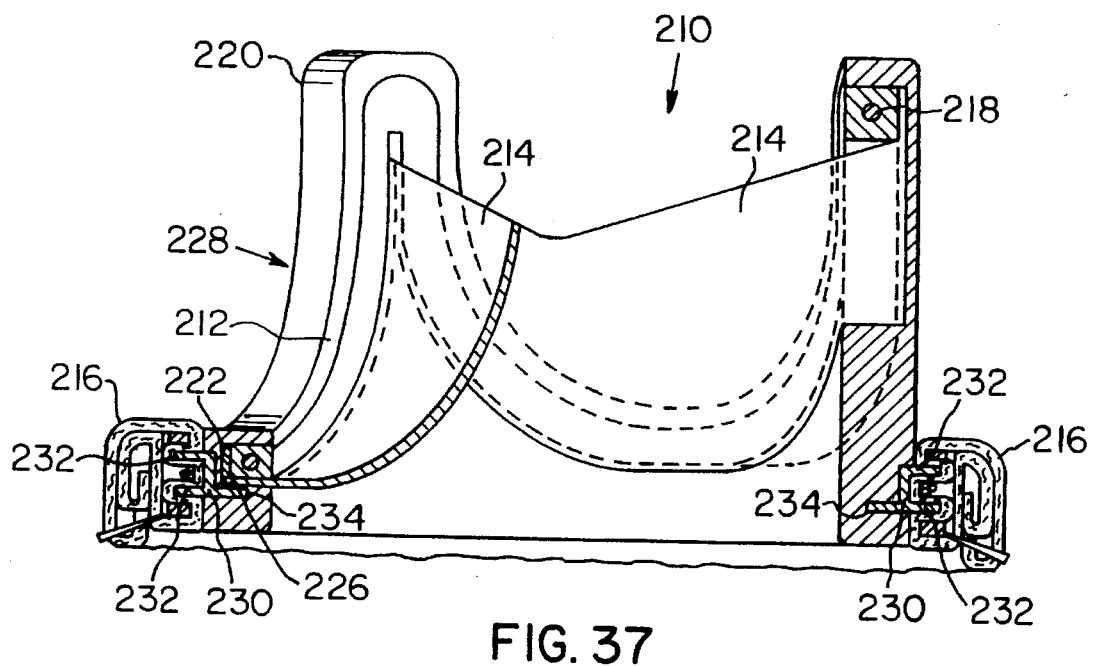
FIG. 37 is a section on line XXXVII—XXXVII of FIG. 36.

FIG. 36 is a plan view of a fourth embodiment of the present heart valve, and FIG. 37 is a section taken along lines XXXVII—XXXVII of FIG. 36. Several structures in the fourth embodiment are identical to those of the third embodiment and these are: the heart valve 210; the stent 212; the leaflets 214; the suture ring 216; the continuous wire 218; the U-shaped members of stent 220; the rectangular outer surface of branch 222; the rectangular member of leaf 226; the hood assembly 228; the ring of hood 230; the external ring flanges 232 and the internal ring flange 234. The same materials are used and apart from the below-described differences unique to the fourth embodiment, features and function should be understood to be the same as those identified for the foregoing embodiments.

The fourth embodiment of the present heart valve is a modification of the third embodiment in that the top free edge of each leaflet 214 is cut down toward the center of the heart valve at an angle of about 27° from the stent toward the center of the valve. The effect of this design modification is to reduce the flat coating surface area of the contiguous sides 224 of leaflets 214, therefore reducing excess leaflet material which otherwise contributes to flag-like flutter of the leaflets as the valve opens and closes. This unwanted flag-like flutter contributes to inefficiency of the valve in the forward flow condition, and its reduction improves overall valve design. The cutting of the leaflets 214 may be completed either after the heart valve is assembled or while the leaflet is still on the mandrel which formed it, and prior to heart valve assembly.

V. Description of the Fifth Embodiment of the Invention

Figure 38:
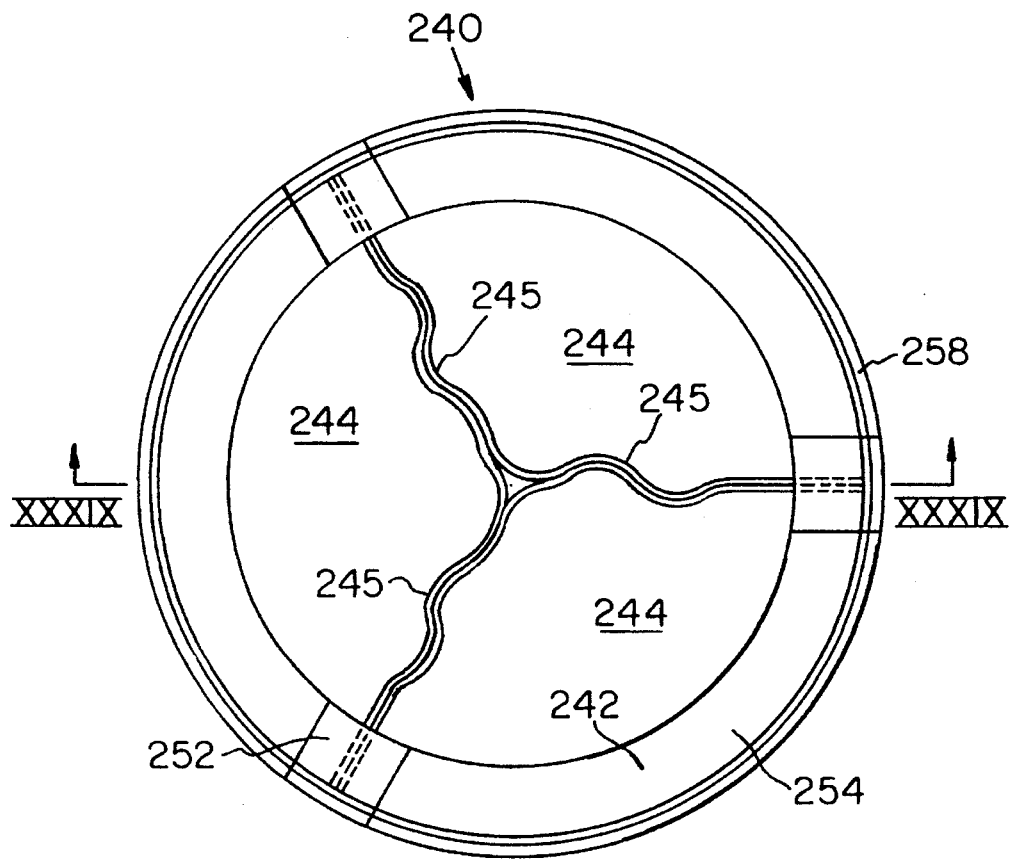
FIG. 38 is a plan view of a heart valve according to a fifth and preferred embodiment of the present invention.
Figure 39:
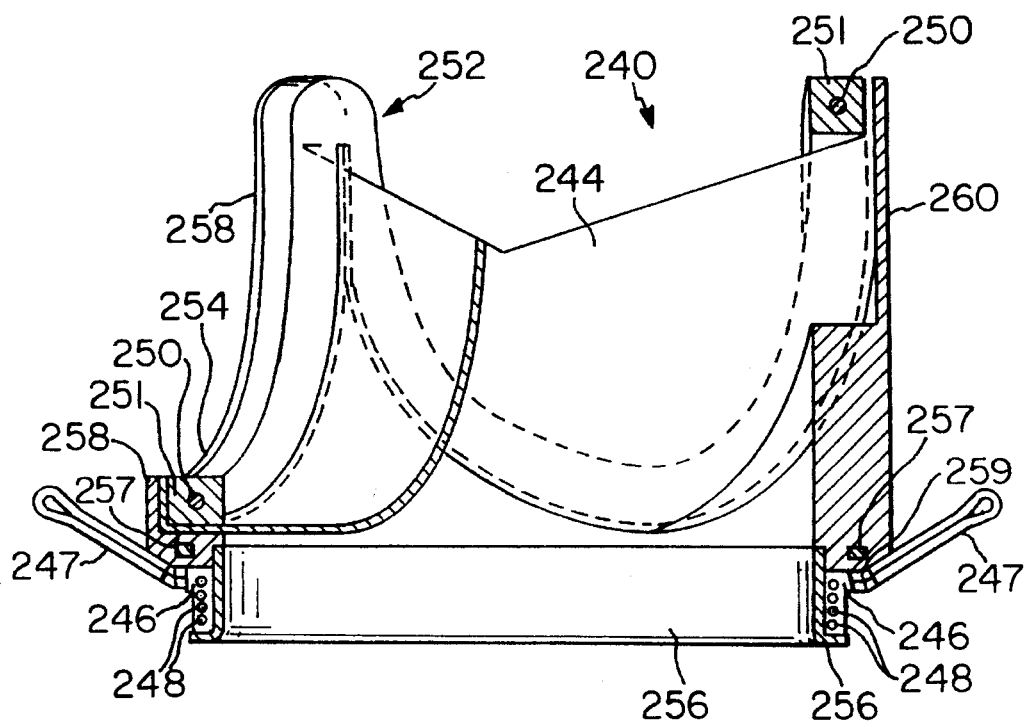
FIG. 39 is a section on line XXXIX—XXXIX of FIG. 38.

FIG. 38 is a plan view of a fifth and preferred embodiment of the present heart valve. FIG. 39 is a section along lines XXXIX—XXXIX of FIG. 38.

FIGS. 38 and 39 illustrate a heart valve 240 having a stent 242 similar to those of the previous embodiments, although it comprises mainly the branches of the other embodiments with a much modified and reduced hood assembly, referred to in this embodiment as the polymer stent cover matrix discussed below. The stent 242 includes the continuous wire 250 and the polymer matrix 251 of stent 242 immediately surrounding the wire 250. The continuous wire 250 and the polymer matrix 251 of stent 242 together comprise the three branches analogous to the branches of the other embodiments. The polymer matrix 251 of stent 242 is rectangular in cross section, as are the branches of the third and fourth embodiments. The continuous wire 250 and its associated polymer matrix 251 form the U-shaped members 252 of stent 242 and the curved interconnecting members 254 of stent 242. The actual wire and polymer materials may be the same as those of the above-described embodiments.

An important feature of the fifth embodiment is the placement and dimension of the metal ring 256. The space interior of the metal ring 256 has the same diameter as does the interior space within the stent 242 when the sinusoidal leaflets 244 are in their open position. This design maximizes blood flow—and minimizes formation of unwanted blood flow currents—for any given valve size. The metal ring 256 is manufactured of any of the surgical steel or titanium alloys known in the surgical implantation art.

The exposed titanium ring preferably is made from ASTM F 67-77 unalloyed titanium for surgical implantation either grade 2, 3 or 4. Titanium alloys such as ASTM F 136-79 titanium 6AL4V for surgical implantation may also be used although they are not preferred. While surgical stainless steels such as AISI grade 316 may be adequate to be used in this application they are not recommended.

The metal ring 256 is adhered to the heart valve 240 by molding it in situ with, or adhering it with an adhesive to, the stent 242 and the polymer stent cover matrix 258. The polymer stent cover matrix 258 is simply a thin (i.e., 0.015 inch thick) outer polymer coating over the stent 242 and the upper region of the metal ring 256 which adheres the stent 242 and the metal ring 256 together into a single unit. If the polymer stent cover matrix 258 is not completely formed in situ with the metal ring 256 and the stent 242, alternatively the polymer ring 259 of the polymer stent cover matrix 258 may be formed in situ with the metal ring 256 and the polymer legs 260 of the polymer stent cover matrix 258 may be bonded into place with one of the adhesives disclosed above. The polymer legs 260 and the polymer ring 259 of the polymer stent cover matrix 258 are shown all together as a single unitary structure in FIG. 39.

The polymer stent cover matrix 258 performs the same basic function as do the hood assemblies of the other described embodiments, but because it is not as massive it reduces the mounting diameter of the heart valve 240 as a whole, to give greater blood flow per unit of orifice area. The upper rim of the metal ring 256 has a plurality of round or rectangular voids spaced circumferentially therearound; these voids allow permeation of the polymer which forms the polymer stent cover matrix 258 to secure the polymer stent cover matrix 258 to the metal ring 256. The voids are visible in FIG. 39 as the polymer-filled areas between adjacent segments of the metal ring 256.

Another important feature of the fifth embodiment is the sinusoidal configuration of the sinusoidal leaflets 244. Although the sinusoidal leaflets 244 of the present embodiment are basically manufactured and adhered to the stent in the same manner as described for the other embodiments (particularly those embodiments in which the "outer surface of branch" is rectangular), the shape of the mandrel and thus the shape of the sinusoidal leaflet 244 differs as follows. The sinusoidal leaflets 244 have contiguous surfaces 245 which have individual lengths greater than those of the leaflets of other embodiments, so that the contiguous surfaces 245 do not merely meet up and touch one another but fit together in a "sinusoidal" configuration which the oversize leaflets take on automatically. This sinusoidal configuration allows the heart valve 240 to close more completely and to avoid even further the above-described unwanted flag-like flutter, so that regurgitation through the valve is minimized to the greatest possible extent. The same sinusoidal configuration also allows the sinusoidal leaflets 244 to open to the greatest extent possible, to allow maximum unimpeded blood flow through the valve in its open position.

Mandrels 1larger than required to trisect the valve orifice are used to create the sinusoidal shaped leaflets. To accomplish this end the leaflet mandrels are enlarged—increasing the distance from outside radius of the valve to the center point of the valve orifice so that the center apex of the leaflet is actually extending past the center of the valve. In the modified mandrel, the angle measured along the flats of the mandrel now measures 110° rather than 120° in the previous mandrel which trisected the valve without excess material. When viewing the valve from the out flow side of the valve, the arc created by the outside edge of the stent where the leaflet is attached remains the same regardless of whether the leaflets are sinusoidal or just meet precisely to trisect the orifice.

The above-described improvement yielding the sinusoidal leaflets 244 was accomplished by producing a leaflet which has as its radius lengths from the center of the orifice a dimension equal to one third of the circumference of the inside diameter of the orifice. The problem with an orifice with three leaflets that meet perfectly in the center of the orifice is that a restricted or stenotic orifice is formed by the top edge of the leaflets rendering the actual orifice cross sectional area smaller by approximately 10%, but the sinusoidal leaflets of the fifth embodiment completely overcome this 10% orifice reduction problem.

By way of example, a one inch diameter orifice has a cross sectional area of $\pi D^2/4 = 0.7854$ sq. inch. The sum of the six radii of the leaflets can be translated into a circle with a circumference of 3.0 inches, a diameter of 0.955 inch, and an area of 0.7162 sq. inch. The resulting ratio of cross sectional areas is 0.7162/0.7854=0.91 or a reduction of the cross sectional area by 9%. The actual resulting pressure drop is a ratio of the squares of the diameters since the pressure drop scales with area.

A second benefit of the larger leaflet size is that when viewed axially (see FIG. 38), the coating surfaces of the leaflets 244 meet in a sinusoidal shape. When finite element analysis is performed on this leaflet shape the peak stresses on the leaflet are reduced by a factor of approximately two and stresses are also distributed in a wider area away from the top edge of the leaflet. This reduction in stress allows the valve leaflets to have a longer flex fatigue life.

The metal ring 256 is surrounded by a suture ring 246 having a suture cuff 247; the suture ring 246 is tied around the metal ring 256 with suture threads 248 (more than the four suture threads 248 shown may be used—up to eight or more). The suture ring, suture cuff and suture threads are made of materials known in the art, and the other structures of the fifth embodiment may be made of the same materials as are discussed above in the context of the other embodiments of the invention.

Referring now to FIGS. 34–39, dimensions are generally the same as those dimensions shown in FIGS. 1–33 (with the exception of the comparative thicknesses of the bulkier hood assemblies versus the thinner polymer stent cover matrix of FIG. 39), although those dimensions are exemplary only. Heart valves must be manufactured in a variety of sizes to accommodate heart size which varies from patient to patient.

It is desirable that deterioration of material performance due to calcification and/or environmental stress cracking of the stent and the hood of the heart valve, and particularly of the leaflets, be suppressed. It has been demonstrated[1,2] that the formation of adherent thrombic material and its subsequent dystrophic degeneration is the initial step in the evolution of surface calcification in polymeric membranes. In the case of polyether based segmented polyurethanes, it has been documented[3,4] that the in vivo biological deposition and subsequent foreign body attack of the predominant ether linkages, especially in those regions experiencing stress of flexure, lead to the formation of microfissures in the material's surface. These surface defects encourage the deposition of thrombus, thus favoring calcification, as well as leading to the development of macroscopic cracks, which ultimately result in the premature failure of the prosthetic valve.

The selection of the appropriate segmented polyurethane chemical microstructure will eliminate environment stress cracking by removal of the chemically weak entities and by replacement thereof with more chemically robust structures. Thus, this invention suppresses degradation of the valve materials by eliminating the above mechanisms that lead to dystrophic calcification. The preferred composition of the biocompatible polymeric material in this invention is a segmented polyurethane elastomer comprised of a non-ether based microstructure such as, but not limited to, a poly(alkyl carbonate). Biocompatable materials such as polycarbonate based polyurethane elastomers have been shown[5,6] to be inherently anti-thrombogenic and resistant to in vivo environmental stress cracking. This invention utilizes these characteristics to provide for enhanced valve durability through improved calcification resistance.

REFERENCES

1. S. L. Hilbert, V. J. Ferrans, Y. Tomita, E. E. Eidbo, M. Jones, Evaluation of explanted polyurethane trileaflet cardiac valve prostheses, *J Thorac Cardiovas Surg*, 94, 419–429 (1987).
2. H. Harasaki, A. Moritz, N. Uchida, J-F. Chen, J. T. McMahon, T. M. Richards, W. A. Smith, S. Murabayashi, H. E. Kambic, R. J. Kiraly, Y. Nose, Initiation and Growth of Calcification in a Polyurethane-coated Blood Pump, *Trans Am Soc Artif Intern Organs*, 33, 643–649 (1987).
3. K. Stokes, Polyether Polyurethanes: Biostable or Not?, *J Biomat Appl*, 3, 228–259 (1988)
4. Q. H. Zhao, M. P. Agger, M. Fitzpatrick, J. M. Anderson, A. Hiltner, K. Stokes, P. Urbanski, Cellular Interactions with Biomaterials: In Vivo Cracking of Pre-Stressed Pellethane 2363-80A, *J Biomed Mater Res*, 24, 621–637 (1990).
5. D.C. MacGregor, L. Pinchuk, M. C. Esquivel, J. B. Martin, Jr., G. J. Wilson, Corethane™ as a Substitute for Pellethane for Pacemaker Lead Insulators, *PACE*, 14, 694 (1991).
6. M. Szycher, A. Siciliano, A. M. Reed, Polyurethanes in Medical Devices, *Medical Design and Material*, February 1991, pp. 18–25.

Figure 40:
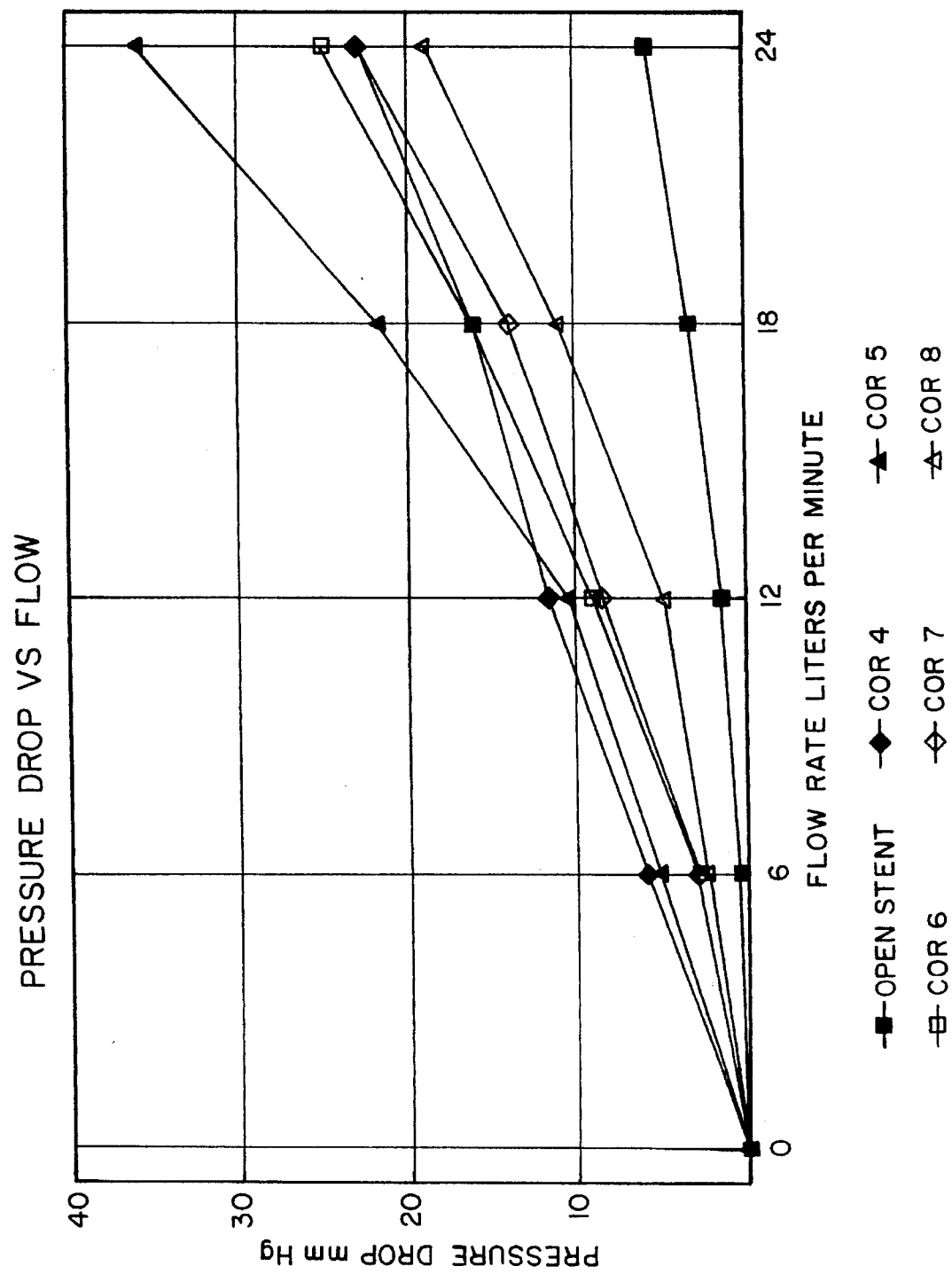
FIG. 40 is a graph illustrating the comparative pressure drop values, at increasing flow rate in liters per minute, for the heart valves illustrated in FIGS. 18–39.

A good way to evaluate the flow advantages of a heart valve is to measure the "pressure drop" which occurs across it. In other words, a poorly performing valve will have a high pressure drop, and an effective valve will have a lower pressure drop. Comparative steady state pressure drop values, in mm Hg, are shown in FIG. 40, for which the Cor 4, Cor 5 and Cor 6 heart valves represent examples of the third embodiment of the present invention, the Cor 7 heart valve is exemplary of the fourth embodiment, and the Cor 8 heart valve represents the fifth and preferred embodiment of the present invention. As is immediately evident upon inspection of the test results for the Cor 8 valve, the fifth embodiment of the present invention gives the lowest pressure drop at the blood flow rate of about 12–24 liters per minute.

The Cor 4, 7 and 8 design valves are typically all 80 A scale durometer (soft) materials. On the other hand, Cor 5 typically utilizes a 60 D scale durometer (harder, stiffer) material and Cor 6 typically uses a 93 A scale durometer (intermediate between 60 D and 80 A materials). Many commercial products of this type, for incorporation in polymeric cardiac prosthesis components, are available. Also, parts can be cast from conventional multi-component liquid resin systems, or can be injection molded from either multi-component resins or polymerized thermoplastic injection moldable pellets.

Although the invention has been described with respect to particular embodiments, all of the embodiments share similarities. Thus, all of the embodiments of the heart valve according to the invention have the following interrelated structures: a metal-reinforced resilient stent of biocompatible material including a plurality of metal-reinforced struts spaced angularly therearound and extending from an annulus; separate flexible leaflets of biocompatible material secured at their outer boundaries to the struts in position to diverge and converge in valve-opening and valve-closing relationship to each other; a biocompatible polymeric covering housing the struts and overlapping the outer boundaries of the leaflets where they are secured to the struts; and a suture ring connected to and encircling the annulus.

The foregoing describes preferred embodiments of the invention and is given by way of example only. The invention is not limited to any of the specific features described herein, but includes all variations thereof within the scope of the appended claims.

What is claimed is:

1. A heart valve comprising a biocompatible, metal-reinforced resilient stent including:
   an annulus, a plurality of metal-reinforced angularly spaced struts extending from said annulus, each of said struts including a metal wire embedded within a biocompatible polymeric material, preformed separate, biocompatible, flexible leaflets having outer boundaries secured to said struts, said leaflets adapted for movement to diverge from each other and converge toward each other to a valve-opening and a valve-closing position, respectively, a biocompatible polymeric covering forming a part of said struts and overlapping said outer boundaries of said leaflets which are secured to said struts, and a suture ring connected to and encircling said annulus.

2. The heart valve according to claim 1 wherein said biocompatible polymeric covering forming a part of said struts and overlapping said outer boundaries of said leaflets further comprises a hood having a plurality of cavities corresponding in number to said struts.

3. The heart valve according to claim 2 wherein each of said leaflets is secured to a portion of each strut spaced from said annulus at a position interior of said hood.

4. The heart valve according to claim 1 wherein said stent includes a frame having a ring of metal having a flange thereon comprising a projection of metal extending generally perpendicularly to said ring, a string wound around said ring wherein said ring has circumferential slots and said string is wound on said ring through said slots in a helical configuration, a covering of biocompatible polymer encasing said frame, said coating impregnating and completely encasing said string and securing said biocompatible polymer to said ring.

5. The heart valve according to claim 1 wherein each of said preformed leaflets secured at their said outer boundaries to said struts is positioned so that sides of each of said leaflets opposite to its said outer boundary abut with sides opposite to said outer boundaries of other of said leaflets.

6. The heart valve according to claim 1 wherein said plurality of metal-reinforced angularly spaced struts are formed by a continuous stent member having a continuous curved wire embedded therein, said continuous stent member mounted adjacent a metal ring forming at least part of said annulus.

7. The heart valve according to claim 1 wherein said biocompatible stent is formed of biocompatible material which consists of a calcification-resistant segmented polyurethane elastomer.

8. The heart valve according to claim 7 wherein said polyurethane demonstrates resistance to in vivo environmental stress cracking.

9. The heart valve according to claim 7 wherein said polyurethane demonstrates resistance to in vivo surface thrombus formation.

10. The heart valve according to claim 6 wherein said metal ring has two external flanges and one internal flange.

11. The heart valve according to claim 6 wherein said metal ring has a single flange having spaced voids formed therein.

12. The heart valve according to claim 1 wherein each of said leaflets has a top free edge angled downwardly from the horizontal toward a center of said heart valve at an angle of about 27°.

13. The heart valve according to claim 1 wherein a region of said leaflets which contacts each other in said valve-closing position is sinusoidal in shape.

14. The heart valve according to claim 6 wherein said metal ring has an interior diameter approximately equal to an interior diameter of said stent, further wherein said stent member is rectangular in section and each of said leaflets has a rectangular member thereon adhered with an adhesive to a rectangular outer surface of a portion of said stent member which is adjacent said leaflet.

15. The heart valve according to claim 1 wherein said annulus includes a metal ring positioned adjacent said plurality of metal-reinforced angularly spaced struts.

16. The heart valve according to claim 15 wherein said metal ring has an inner diameter substantially equal to an inner diameter of said leaflets in said valve-opening position.

17. A heart valve comprising a biocompatible, metal-reinforced resilient stent, said stent including:

an annulus, a plurality of metal-reinforced angularly spaced struts extending from said annulus, and preformed separate, biocompatible, flexible leaflets having outer boundaries secured to said struts, said leaflets adapted for movement to diverge from each other to a valve-opening position and to converge toward each other to a valve-closing position, wherein a region of said leaflets which contacts each other in said valve-closing position is sinusoidal in shape, and wherein each of said leaflets has a length from a center of said heart valve to a interior of said stent equal to one third of the circumference of an inside diameter of said interior of said stent, a biocompatible polymeric covering forming part of said struts and overlapping said outer boundaries of said leaflets which are secured to said struts, and a suture ring connected to and encircling said annulus.

* * * * *